United States Patent [19]

Ratcliff

[11] 4,244,020

[45] Jan. 6, 1981

[54] CALORIC AND/OR CARBOHYDRATE CALCULATOR

[76] Inventor: Lloyd P. Ratcliff, 306 Bayou Oaks Dr., Monroe, La. 71203

[21] Appl. No.: 3,741

[22] Filed: Jan. 15, 1979

[51] Int. Cl.$^3$ .................. G06F 15/42; G01G 19/04
[52] U.S. Cl. .................................. 364/413; 177/25; 364/567; 364/709; 364/715
[58] Field of Search ............... 364/413, 709, 715, 567, 364/705; 177/1, 25

[56] References Cited

U.S. PATENT DOCUMENTS 4,095,274  6/1978  Gordon .............................. 364/413

OTHER PUBLICATIONS

Moran, K. M., "Electronic Diet Controller", *Computer Design*, Aug. 1977, pp. 116-118.

*Primary Examiner*—Errol A. Krass
*Attorney, Agent, or Firm*—Norvell E. Von Behren

[57] ABSTRACT

A calculator for use in calculating the appropriate caloric and/or carbohydrate value of a food or drink item that is to be consumed by the user of the device is disclosed. The calculator utilizes a modified four-basic-function calculator of the type having the functions of addition, subtraction, multiplication and division. This basic calculator has been modified by adding a plurality of first contacts to the calculator which visually indicate alphabetical letters and are connected to numerical contacts in the standard calculator. A plurality of second contacts are numerical in function and indicate pre-determined food and drink items and are electrically connected to the calculator circuit while a plurality of third contacts are multiplier contacts and have located in proximity thereto indications of pre-determined alphabetical letters which correspond to caloric and/or carbohydrate values of varying portions of food and drink items. A fourth contact is electrically connected in the equal circuit of the standard calculator and indicates the wording "calorie" or "carbohydrate".

Also disclosed is a novel method using the novel calculator whereby the calories and/or carbohydrates of a given food and drink item may be quickly determined without resorting to pages and pages of printed material relating to the various values. As a modification of the basic invention, there is disclosed a modified calculator in combination with a weighing scale mechanism, the scale having an exposed dial indicating varying combinations of alphabetical letters.

34 Claims, 10 Drawing Figures

| | 46 / 20 | 48 / 20 | 50 / 20 | 52 / 20 | 54 / 20 | 56 |
|---|---|---|---|---|---|---|
| DRINKS | ☐ CK<br>FRUIT JUICE<br>TABLE WINE | VEG.<br>JUICE | ☐ CJ<br>JIG-80 PRF.<br>WHISKEY | ☐ EA<br>GINGER ALE<br>DESSERT WINE | ☐ EF<br>COLA - BEER<br>ROOT BEER | ☐ GE<br>FRUIT<br>FLAVORS |
| BREADS<br>&<br>CEREALS | ☐ D<br>PRETZEL<br>CRACKER | | ☐ AJ<br>SLICE BREAD<br>PANCAKE | ☐ CK<br>CORN OR RICE<br>CEREALS<br>GRITS | ☐ EK<br>BISCUIT<br>RICE<br>WHEAT CEREAL | ROLL | ☐ GK<br>PIZZA<br>SPAGH.& MTBLS.<br>WAFFLE |
| DESSERTS<br>SWEETS | ☐ CK<br>ANGEL CAKE<br>SIRUP-JELLIES<br>FIG BAR | HARD<br>CANDY | ☐ EK<br>COOKIE<br>CUSTARD<br>ICE CREAM | FRUIT<br>CAKE | ☐ GK<br>GINGER BRD.<br>PLAIN CAKE<br>WITH ICING | ☐ BK<br>PIE | ☐ FK<br>PECAN PIE<br>CANDY BAR |
| FATS<br>OILS<br>DRESSINGS | ☐ G<br>LO-CAL<br>DRESSING | | ☐ F<br>HOME COOKED<br>SALAD DRESS<br>PAT BUTTER | ☐ AE<br>SALAD DRESS<br>GRAVY | ☐ AD<br>MAYONNAISE<br>PEANUT BUTTER | ☐ CA<br>SALAD OIL |
| MEATS | ☐ AD<br>BACON, CLAM<br>OYSTER, NUTS<br>LUNCH MEAT | EGG | ☐ CJ<br>BROILED FISH<br>MEAT LOAF<br>CORNED BEEF | SHRIMP | ☐ EG<br>SAUSAGE<br>BROIL-TURK.CHIC.<br>FRIED FISH | BEEF<br>STEW | ☐ GC<br>CHILI, HAM<br>VEAL CUTLET<br>LEAN MEATS | LIVER | ☐ JF<br>MEAT W/FAT<br>STEAKS/CHOPS<br>POT PIES |
| MILK<br>PRODUCTS | ☐ CJ<br>BUTTERMILK<br>SKIM<br>SLICE CHEESE | | ☐ EF<br>YOGHURT<br>CUSTARD<br>SHERBET | ☐ JK<br>EVAPORATED<br>WHOLE<br>CHOC. FLAV. | ☐ BE<br>SOUR CREAM<br>COCOA<br>CHOC. SODA | ☐ FD<br>MALT<br>CHOCOLATE<br>SHAKE |
| SNACKS | ☐ AK<br>OLIVES<br>PICKELS<br>POPCORN | | ☐ CK<br>POTATO CHIPS | ☐ EK<br>FRENCH FRIES<br>CORN CHIPS | ☐ CK<br>PIZZA SLICE<br>DONUT | ☐ JK<br>HOT DOG<br>HAMBURGER |
| SOUPS | ☐ B<br>CHICKEN<br>W/RICE<br>OR NOODLE | BROTH | ☐ H<br>BEEF NOODLE<br>TOMATO<br>CLAM CHOWD. | VEG. | ☐ AE<br>ASPARAGUS<br>MINESTRONE<br>VEG. W/BEEF | ☐ AH<br>MUSHROOM<br>SPLIT PEA | ☐ CJ<br>TOMATO, MILK<br>BEAN W/PORK<br>OYSTER STEW |
| VEGETABLE<br>& FRUITS | ☐ E<br>RAW<br>VEGETABLES | COOKED<br>GREEN<br>BEANS | ☐ B<br>BOILED<br>VEGETABLES | ☐ AC<br>BAKE POTATO<br>DRIED BEANS<br>CORN ON COB | RAW<br>FRUIT | ☐ AD<br>FRENCH FRIES<br>SWEET POTATOE | COOK<br>FRUIT | ☐ CE<br>AVACODOS<br>PRE-SWEET<br>COOK FRUITS | DATE<br>RAISN |

CALORIC

*Fig. 3*

| | 46 / 20 / 48 | 20 / 50 | 20 / 52 | 20 / 54 | 20 / 56 |
|---|---|---|---|---|---|
| DRINKS | ☐ K<br>JIG-80 PRF.<br>WHISKEY | ☐ A<br>WINE GLASS<br>TABLE WINE | ☐ E<br>DESSERT WINE<br>FRUIT FLAVOR<br>DRINKS | ☐ J<br>COLA - BEER<br>ROOT BEER<br>GINGER ALE | ☐ D<br>CIDER<br>LEMONADE |
| BREADS & CEREALS | ☐ A<br>PRETZEL<br>CRACKER | ☐ C<br>PANCAKE | ☐ E<br>SLICE BREAD<br>CEREALS | ☐ G<br>BRAN CER.<br>BISCUIT<br>ROLL | ☐ B<br>RICE<br>SPAGH & MTBLS.<br>WAFFLE |
| DESSERTS | ☐ C<br>HARD CANDY<br>COOKIE | ☐ E<br>FIG BAR<br>CUSTARD<br>SIRUP-JELLY | ☐ J<br>ICE CREAM | ☐ B<br>ANGEL CAKE<br>SHERBET | ☐ F<br>CANDY BAR<br>PIE |
| FATS OILS DRESSINGS | ☐ K<br>MAYONNAISE | ☐ K<br>PAT BUTTER | ☐ K<br>SALAD OIL | ☐ LJ<br>SALAD DRESS.<br>GRAVY | ☐ LJ<br>PEANUT<br>BUTTER |
| MEATS | ☐ K  CAN FISH<br>FOWL, LUNCH MT.<br>CORN BF. BOIL EGG<br>STEAK/CHOPS | ☐ LJ  CLAM<br>EGG OMEL.<br>BACON, MT.LOAF<br>SAUSAGE | ☐ A<br>SHRIMP<br>FRIED FISH | ☐ C<br>OYSTER, NUTS<br>LIVER, CHILI<br>BEEF STEW | ☐ G<br>DRIED BEANS<br>POT PIES |
| MILK PRODUCTS | ☐ LC<br>SLICE CHEESE<br>SOUR CREAM | ☐ C<br>SKIM | ☐ E<br>BUTTERMILK<br>WHOLE<br>CONDENSED | ☐ J<br>CHOCOLATE | ☐ B<br>SHERBET<br>MALT<br>SHAKE |
| SNACKS | ☐ A<br>PICKEL<br>OLIVES | ☐ C<br>POPCORN | ☐ E<br>POTATO<br>CHIPS | ☐ G<br>FRENCH FRIES<br>CORN CHIPS | ☐ J<br>PIZZA, DONUT<br>HOT DOG<br>HAMBURGER |
| SOUPS | ☐ K<br>BOUILLION | ☐ LJ<br>BROTH | ☐ A<br>CHICKEN W/RICE<br>BEEF NOODLE<br>MUSHROOM | ☐ C<br>CLAM CHOWD<br>TOMATO<br>VEGETABLE | ☐ E<br>BEAN<br>PEA |
| VEGETABLE & FRUITS | ☐ LJ<br>RAW VEGS.<br>COOKED<br>GRN. BEANS | ☐ A<br>COOKED<br>GREENS | ☐ C<br>RAW FRUIT<br>COOKED VEG. | ☐ E<br>COOKED FRUIT<br>DRIED BEANS | ☐ G<br>PRE-SWEET COOK<br>FRUIT<br>SWEET POTATO |

CARBOHYDRATE

*Fig. 4*

*Fig. 8* CALORIC

|  | 118 | 120 | 122 | 124 | 126 |
|---|---|---|---|---|---|
| ☐ DRINKS | VEG. JUICE-E FRUIT JUICE-AE TABLE WINE-G | JIG. 80 PRF. WHISKEY-DB | GINGER ALE-H DESSERT WINE-GK | COLA-AG BEER-AC ROOT BEER-AC | FRUIT FLAVOR DRINKS-AG |
| ☐ BREADS | PRETZEL-FK CRACKER-AEE | BREAD-DK PANCAKE-GK | CORN OR RICE CEREAL-AJ GRITS-F | ROLL-B BISCUIT-JC RICE-CE WHEAT CER.-AKJ | PIZZA-FJ SPAGH.&MTBL-CF WAFFLE-DK |
| ☐ DESSERTS | HARD CANDY-AAK ANGEL CAKE-AEJ SIRUP, HK JELLY-JD FIG BAR-BJ | FRUIT CAKE-AAK COOKIE-AKK CUSTARD-EK ICE CREAM-CF | GINGER BRD-AKK PLAIN CAKE W/ICING-AAE | PIE-JC | PECAN PIE-BB CANDY BAR-AGJ |
| ☐ FATS | LO-CAL DRESSING-EK | HOME COOKED SALAD DRESS-AJK BUTTER-AGK | SALAD DRESS-AEK GRAVY-CF | MAYONNAISE-CKK PEANUT BUTT.-ACB | SALAD OIL-CGK |
| ☐ MEATS | EGG-JK BACON-JC CLAM-CC OYSTER-AJ NUTS-CDK LUNCH MEAT-FJ | SHRIMP-EE BROIL. FISH-BD MEAT LOAF-BJ CORN BEEF-JC | BEEF STEW-AG SAUSAGE-BE BROIL.TURK,CHIC-JK FRIED FISH-JK | LIVER-BJ CHILI-EJ, HAM-FC VEAL CUTLET-BC LEAN MEAT-DJ | MEAT W/FAT-FJ STEAK/CHOPS-AAK POT PIE-JJ |
| ☐ MILK PRODUCTS | BUTTERMILK-AA SKIM-AA CHEESE-AAJ | YOGHURT-AD CUSTARD-JA SHERBET-CC | EVAPORATED-JK WHOLE-CK CHOC. FLAV.-CD | SOUR CREAM-JK COCOA-EK CHOC. SODA-CK | MALT-EA CHOC. SHAKE-GE |
| ☐ SNACKS | CHIVES-A PICKELS-AK POPCORN-AKF | POTATO CHIPS-CEK | FRENCH FRIES-EK CORN CHIPS-FK | PIZZA-FJ DONUT-ACD | HOT DOG-AKK HAMBURGER-FJ |
| ☐ SOUPS | BROTH-AK CHICKEN W/RICE OR NOODLE-D | VEGETABLE-AA BEEF NOODLE-H TOMATO-AC CLAM CHOWD-AA | ASPARAGUS-AG MINESTRONE-AG VEG W/BEEF-AJ | MUSHROOM-AF SPLIT PEA-AF | TOMATO MILK-CE BEAN W/PORK-CE OYSTER STEW-AB |
| ☐ VEGETABLES FRUITS | GREEN BEANS-E RAW VEGETABLES-E | BOILED VEGETABLES-AK | RAW FRUIT-AD BAKE POTATO-AJ DRIED BEANS-AE CORN ON COB-AE | COOK.FRUIT-AD FRENCH FRIES-FK SWT. POTATO-CD | DATE-GJ RAISN-AKD AVACODOS-EF PRE-SWEET COOK FRUIT-CC |

Fig. 9 — CARBOHYDRATE

| | 118 | 120 | 122 | 124 | 126 |
|---|---|---|---|---|---|
| ☐ DRINKS | JIG·80 PRF. WHISKEY-K | TABLE WINE-CLE | DESSERT WINE-G FRUIT FLAVOR-E | COLA-ELE BEER-ALJ ROOT BEER-ALJ GINGER ALE-CLD | CIDER-LEE LEMONADE-ELJ |
| ☐ BREADS | PRETZEL-LA CRACKER-JA | PANCAKE-LJE | SLICE BRD-AC CEREALS-CK | BRAN CER.-AF BISCUIT-H ROLL-CK | RICE-G SPAGH.&MTBL-G WAFFLE-AK |
| ☐ DESSERTS | HARD CANDY-A COOKIE-EK | FIG BAR-AJ CUSTARD-E SIRUP-AD JELLY-AB | ICE CREAM-G | ANGEL CAKE-CC SHERBET-J | CANDY BAR-AB PIE-D |
| ☐ FATS | MAYONNAISE-K | BUTTER-K | SALAD OIL-K | SALAD DESS.-G GRAVY-G | PEANUT BUTTER-B |
| ☐ MEATS | CAN FISH-K FOWL-K LUNCH MT.-K CORN BEEF-K BOIL EGG-K STEAK/CHOP-K | CLAM-BLA EGG OMEL-C BACON-A MT. LOAF-A SAUSAGE-A | SHRIMP-A FRIED FISH-C | OYSTER-C NUTS-C LIVER-A CHILI-E BEEF STEW-E | DRIED BEANS-B POT PIES-J |
| ☐ MILK PRODUCTS | CHEESE-LJ SOUR CREAM-A | SKIM-ALD | BUTTERMILK-ALD WHOLE-ALJ CONDENSED-E | CHOCOLATE-E | SHERBET-HLE MALT-E SHAKE-G |
| ☐ SNACKS | PICKEL-A OLIVES-C | POPCORN-EK | POTATO CHIPS-CK | FRENCH FRIES-BLD CORN CHIPS-CK | PIZZA-AG DO-NUT-AC HOT DOG-G HAMBURGER-G |
| ☐ SOUPS | BOUILLION-K | BROTH-LD | CHICKEN RICE-CLE BEEF NOODLE-C MUSHROOM-E | CLAM CHOWD-ELE TOMATO-B VEGETABLE-GLE | BEAN-BLE PEA-F |
| ☐ VEGETABLES FRUITS | RAW VEG.-C GREEN BEANS-A | GREENS-LF | RAW FRUIT-G COOK. VEG.-C | COOK.FRUIT-B DRIED BEAN-D | PRE-SWEET COOK.FRUIT-H SWEET POTATO-B |

CALORIC AND/OR CARBOHYDRATE CALCULATOR

BACKGROUND OF THE INVENTION

This invention relates generally to calculators and more particularly to a new and novel calculator improvement whereby a person is able to quickly determine the caloric and/or carbohydrate value of a given portion of food or drink without resorting to endless tables as is the usual practice.

It is a recognized fact that the many overweight people in the world are constantly trying to lose weight by various diets and by restricting their caloric and/or carbohydrate intake.

One of the most popular ways of restricting one's diet is to purchase a lengthy book listing every known portion and type of food along with the caloric and/or carbohydrate value. Thereafter the dieter resorts to looking up the appropriate food or drink in the charts contained therein and generally either tries to remember the value and mentally adds it to other values of consumable items or else writes down the value on a separate piece of paper as the items are consumed. It can be seen that this method, while being accurate, can be very burdensome to many people, especially business men and women who travel extensively and must eat out in restaurants during their trips.

SUMMARY OF THE INVENTION

In order to overcome the problems inherent in the beforementioned methods for accomplishing the objectives, there has been provided by the applicant's invention a new and improved calculator which combines in a new and unusual way a standard basic four-function calculator with the beforementioned caloric and/or carbohydrate tables. The applicant's calculator allows the user of the device to be able to quickly calculate the appropriate caloric and/or carbohydrate value either prior to purchasing the food or drink item or after purchasing the item. In addition, it allows the user of the device to tabulate the caloric and/or carbohydrate value of each item which he purchases in order to be able to quickly ascertain his total intake of calories or carbohydrates.

The calculator comprises a standard numerical basic four-function calculator having addition, subtraction, multiplication and division and contains a modified calculator keyboard which has a plurality of first, second and third groups of contacts and at least one fourth contact whereby through the use of these four groups of contacts, the necessary calculation is completed.

The plurality of first contacts are numerical in function and indicate visually alphabetical letters which represent a numerical value. The first contact is electrically connected to the standard electrical circuit of the calculator so that each visual alphabetical letter represents and contacts, when pushed, a different numeral from zero to nine in the calculator electrical circuit. The plurality of second contacts are numerical in function and indicate pre-determined food and drink items and are electrically connected in the calculator electrical circuit in such a manner that each second contact has a pre-determined numerical value and each second contact is electrically connected in parallel to other similar second numerical contacts and to the similar first numerical contact in the standard numerical calculator.

The plurality of third contacts are multiplier contacts and are positioned so that there is located in proximity to each contact indications of pre-determined alphabetical letters which correspond to caloric and/or carbohydrate values of varying portions of food and drink items. The third contacts are then electrically connected together and to the standard calculator circuit multiplier contact. At least one fourth contact is provided in the modified keyboard which is an equal contact and is connected to the standard electrical circuit with the contact indicating either the wording "calories" or "carbohydrates" or a combination of the two.

By a manipulation of the various contacts as will be described hereinafter when discussing the method of the subject invention, there will then be calculated by the device the appropriate caloric and/or carbohydrate value of the food or drink item to be consumed.

In a modification of the invention, there is provided a calculator in combination with a weighing mechanism having an exposed dial indicating varying combinations of alphabetical letters and further having a weighing platform positioned on the exterior of the calculator/scale case. By modifying the basic calculator as described hereinafter, the user of the device can simply weigh a given portion of food and/or drink and then accurately and quickly calculate the caloric and/or carbohydrate value of the item.

Accordingly, it is an object and advantage of the invention to provide an improved calculator having a modified keyboard which allows the user of the device to quickly calculate the caloric and/or carbohydrate value of the food consumed without resorting to lengthy tables as is the past practice.

Another object and advantage of the invention is to provide a new and novel calculator which combines a basic Four-function calculator having addition, subtraction, multiplication and division circuitry with a book or table having numerical values representing caloric and/or carbohydrate values of various food and drink items.

Still yet another object and advantage of the invention is to provide a new and novel calculator which may be used by business men and women while traveling and eating out in restaurants without having to resort to lengthy charts or bulky books in order to find the appropriate caloric and/or carbohydrate value.

Another object and advantage of the invention is to provide a new and novel calculator which may be used with a modified weighing scale by a housewife or cook to quickly and accurately calculate the caloric and/or carbohydrate value of a food and/or drink item.

These and other objects and advantages of the invention will become apparent from a review of the drawings of the invention and from a reading of the description of the preferred embodiment.

BRIEF DESCRIPTION OF THE DRAWING

For a further understanding of the nature and objects of the present invention, reference should be had to the accompanying drawings, in which like parts are given like reference numerals and wherein:

FIG. 3 is an enlarged view of a portion of the modified calculator keyboard showing the plurality of third contacts when used with a caloric keyboard and further showing the indications of pre-determined alphabetical letters located in proximity to the contacts which correspond to caloric values of varying portions of food and drink items;

FIG. 4 is an enlarged view of a portion of the modified calculator keyboard showing the plurality of fourth contacts when used with a carbohydrate keyboard and further showing the indications of pre-determined alphabetical letters located in proximity to the third contacts which correspond to carbohydrate values of varying portions of food and drink items;

FIG. 8 is an enlarged view of a portion of the modified caloric calculator keyboard of the applicant's invention as shown in FIG. 6;

FIG. 9 is an enlarged view of a portion of the modified carbohydrate calculator keyboard of the applicant's invention as shown in FIG. 6.

BRIEF DESCRIPTION OF THE PREFERRED EMBODIMENT

Figure 1:
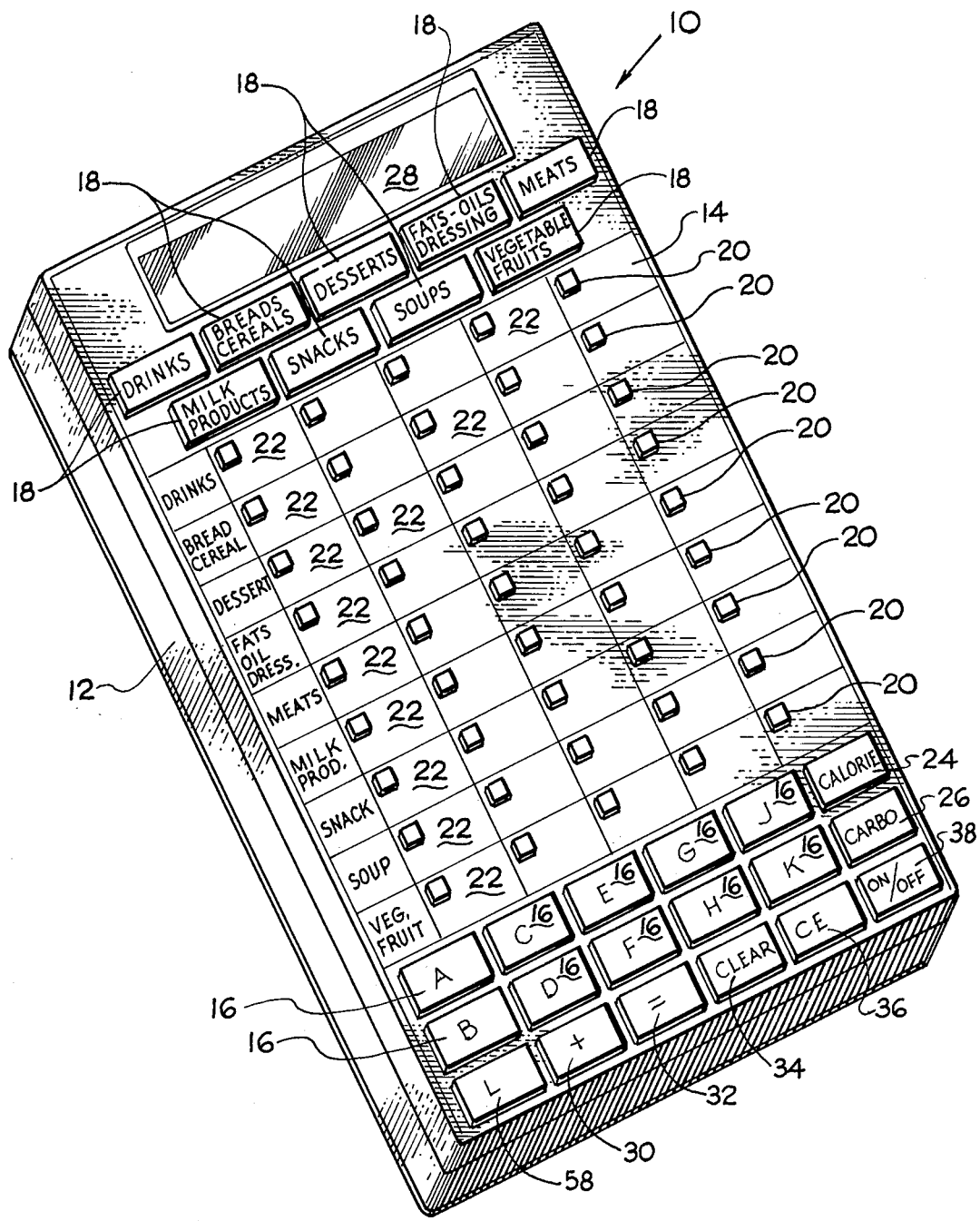
FIG. 1 is a perspective view of the applicant's new and improved caloric and/or carbohydrate calculator showing the modified calculator keyboard having the plurality of first, second, third and fourth groups of contacts.

Referring now to the drawing FIGS. 1-5 in general and in particular to FIG. 1 of the drawings, there is shown a perspective view of the applicant's new and improved calculator which may be used for calculating the appropriate caloric and/or carbohydrate value of a food or drink item and is shown generally by the numeral 10 which comprises a calculator case 12 having contained therein a standard numerical calculator electrical operation circuit of the type having the usual four-basic-functions of addition, subtraction, multiplication and division. Typical calculators of this type would be the calculator manufactured by Texas Instrument Company No. TI-1680, No. TI-30SP, No. TI-1025, No. TI-1000 and other similar calculators manufactured by the same company and also by other companies of the type readily available in the marketplace today.

The applicant's new and improved calculator contains a modified calculator keyboard 14 which has a plurality of first contacts 16 which are numerical in function as will be described hereinafter and indicate visually alphabetical letters as shown in FIG. 1. A plurality of second contacts 18 are numerical in function as will be explained hereinafter and indicate predetermined food and drink items as shown in FIG. 1. A plurality of third contacts 20 are multiplier contacts as will be hereinafter described and have located in proximity thereto indications of predetermined alphabetical letters corresponding to caloric and/or carbohydrate values of varying portions of food and drink items. In FIG. 1 of the drawing the indications are shown by the numeral 22 and for a further clarification of the indications, reference will be made to FIGS. 3 and 4 to be described hereinafter to show specifically the various indications of the food and drink item as well as the pre-determined alphabetical letters.

In the calculator shown in FIG. 1, the plurality of second contacts indicating food and drink items number 9 and the plurality of third contacts indicating indications of alphabetical letters numbers a total of 45. It is within the spirit and scope of the invention that the total number of first, second, third and fourth contacts will vary according to the design of the manufacturer of the calculator and the applicant is not to be limited to the exact numbers shown in the drawings.

In the calculator shown in FIG. 1, there is also provided a fourth contact 24 and a fourth contact 26 with the fourth contact 24 indicating the wording calories while the fourth contact 26 indicates the word carbohydrates. The plurality of fourth contacts 24 and 26 are equal contacts in the electrical circuit as will be described hereinafter and will function in the manner to be described. The applicant's calculator also contains a standard numerical readout 28 of the type containing a plurality of visual digital numbers which are illuminated from the standard electrical circuit by means of a self-contained battery positioned within the calculator case 12 or by means of solar cells also positioned in the case 12 in a manner to collect natural or artificial light.

A fifth contact 30 is positioned on the keyboard and indicates a plus while another fifth contact 32 is positioned on the keyboard and indicates an equal with the plus contact 30 being electrically connected to the memory add circuit of the standard numerical calculator as will be hereinafter described and the equal contact 32 being electrically connected to the equal circuit of the standard numerical calculator as will also be hereinafter described.

Completing the keyboard of the applicant's new and improved calculator would be a standard contact 34 indicating a CLEAR and a standard contact 36 indicating a CE with these two contacts functioning in the standard way to clear any errors or to clear the entire keyboard as is used in the standard calculator circuit. An on and off contact 38 is also provided on the applicant's calculator keyboard to turn the calculator on and to turn it off as desired by the user of the device.

Figure 2:
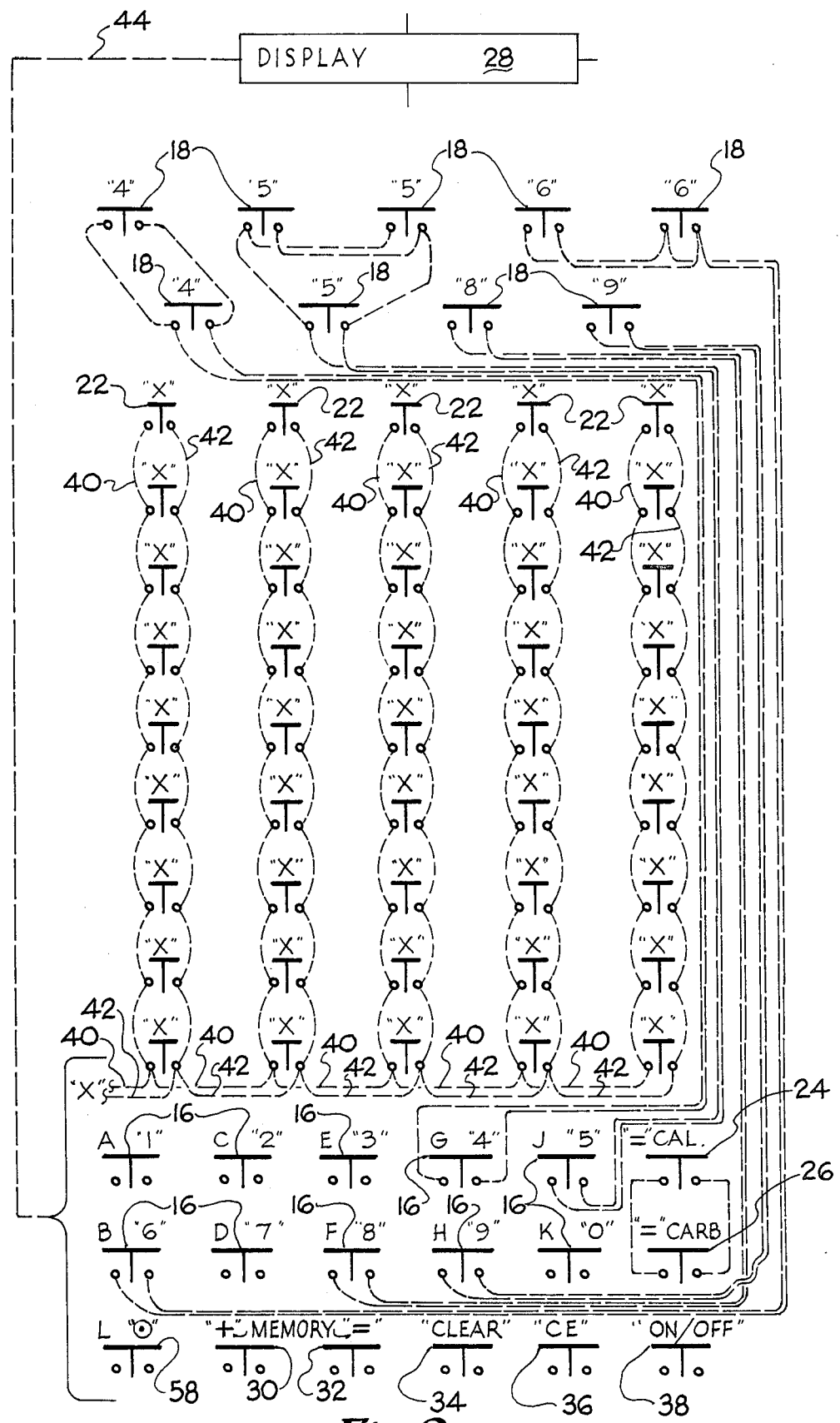
FIG. 2 is a schematic view of the electrical circuitry modifications necessary to modify the standard numerical calculator electrical operation circuit so that the modified calculator keyboard shown in FIG. 1 may be utilized.

Referring now to FIG. 2 of the drawing, there is shown a schematic view of the electrical contacts of the various contacts hereinbefore described and showing how they would be electrically connected to each other in order to function in the manner hereinafter described. In FIG. 2 of the drawing, the various contacts are positioned on the modified calculator keyboard as shown in FIG. 1 of the drawing. In FIG. 2 of the drawing, there is indicated above each contact the numerical number or function of that particular contact in the operation of the calculator, and it can be seen, for example, that the first contacts 16 are the standard numerical contacts of the standard numerical calculator circuitry and number from 0 to 9 as is common in the calculators before mentioned. There is also shown a letter beside each numerical value of the first contacts 16 which would correspond to the letter that would be actually indicated on the contact key as shown in FIG. 1 of the drawing.

The plurality of second contacts 18 are numerical in function, and the numerical value of each second contact 18 is indicated in FIG. 2 of the drawing position on the respective second contact. It can be seen that the actual keyboard indication on the second contact would be as shown in FIG. 1 of the drawing with the respective keys indicating food and drink items and not the numerical value.

Each third contact 22 is a multiplier contact as indicated by the small x positioned above the contact in FIG. 2 and is electrically connected in parallel to each other by lines 40 and 42 and to the multiplier circuit of the standard numerical keyboard. It will also be seen by referring to FIG. 2 of the drawing that each of the numerical second contacts 18 would be electrically connected in parallel to other similar numerical second contacts and to the similar first numerical contact in their standard numerical calculator circuit. While it is not shown on the schematic, it is to be understood that the connection of the plurality of first electrical contacts 16 as well as the contacts 24, 26, 30, 32, 34, 36 and 38 would be electrically connected to their counterpart in the standard numerical calculator circuit. It can also be seen that the contact 24 which would indicate the word "calories" as shown in FIG. 1 of the drawing would be an equal contact while the contact 26, which would indicate the word "carbohydrates", would also be an equal contact, and these two contacts would be connected to their counterpart in the standard numerical circuit.

The digital readout 28 would also be connected by means of the line or lines 44 to the respective calculator circuitry thus completing the total circuitry for the modified keyboard used in the applicant's calculator.

The readout 28 in the preferred embodiment would be modified to register numbers only at the end of a selection sequence whenever the "=" contact 32, the "calorie" contact 24 or the "carbo" contact 26 was punched. This modification would change the standard calculator in a manner such that the number would appear at the end of the selection sequence and not as each contact was pushed.

This modification would tend to make the selection process less confusing to the user of the device but it is within the spirit and scope of the invention that the standard readout sequence could also be used.

By referring to FIGS. 1 and 2 together as well as the hereinbefore described materials relating to those figures, it should be apparent that the applicant's new and novel calculator basically uses the functions of the standard calculator, with a totally modified keyboard having visual indications of food and drink items and visual indication of alphabetical letters in combination with a large plurality of multiplier keys having visual indications contained either thereon or beside the respective multiplier key. Before describing the operation of the applicant's calculator, reference should now be made to FIGS. 3 and 4 of the drawing which would represent the face-place of the applicant's keyboard in the area of the plurality of third contacts 20 whenever a calculator were constructed which would be designed for use to calculate calories only. In a similar manner, the drawing shown in FIG. 4 would represent the face-place of a calculator which would be designed to be used as a calculator for figuring carbohydrates only. When it would be desirous to manufacture a calculator capable of calculating both calories and carbohydrates, it is within the spirit and scope of the invention that the face-plate for the keyboard surrounding the contacts 20 would be a combination of the face-plate shown in FIGS. 3 and 4 of the drawing.

It can be seen by referring to both FIGS. 3 and 4 that there is provided in the face-plate a left-hand vertical column 46 having indications of various food and drink items. Each food and drink item mentioned in column 46 would then be related horizontally to the appropriate specific item which would be printed on the face-plate and would have an appropriate alphabetical letter or letters printed in proximity to the key or in an alternate embodiment on the face of the key. For example, when referring to column 46 and the first drink item, it will be seen that there are listed three (3) common drinks available to the user. These drinks would be vegetable juice, fruit juice and table wine, and there would be indicated the alphabetical letters CK in proximity to the contact 20. Immediately to the right of this would be represented a drink item of a jigger of 80-proof whiskey with the alphabetical indication CJ in proximity to the key 20. In a like manner, other food and drink items are indicated in the various columns and above each item would be indicated an alphabetical designation which will be described hereinafter in describing the operation of the calculator.

When manufacturing the face-plate and positioning the various food and drink items on the face-plate, it may be desirous to group the food and drink items in such a manner that the lower caloric or carbohydrate items would be all positioned vertically in one column with the next higher caloric or carbohydrate values being positioned next to them. For example, the lower caloric and carbohydrate values may all be positioned in the vertical column 48 while the next higher caloric and carbohydrate values would be positioned in the column 50 with column 52, 54 and 56 each representing higher caloric and carbohydrate values. It may also be desirous to color-code the respective vertical columns 48–56 in such a manner to visually indicate to the user of the device that the items in that particular column have either a low or a high caloric or carbohydrate value or some intermediate value between. For example, it may be desirous to color-code the vertical column 48 in a dark green to indicate a low caloric or carbohydrate value while the vertical column 50 would be color-coded in a light green and the vertical column 52 would be color-coded yellow. In a like manner, the vertical column 54 would be color-coded light red and the vertical column 56 would be color-coded red to indicate the highest caloric or carbohydrate values of the items being chosen. In this manner it can be seen by the use of the color-coding, the user of the device can instantly see when he is selecting and calculating a higher value food and he may want to re-evaluate his selection to a lower caloric or carbohydrate value.

Figure 5:
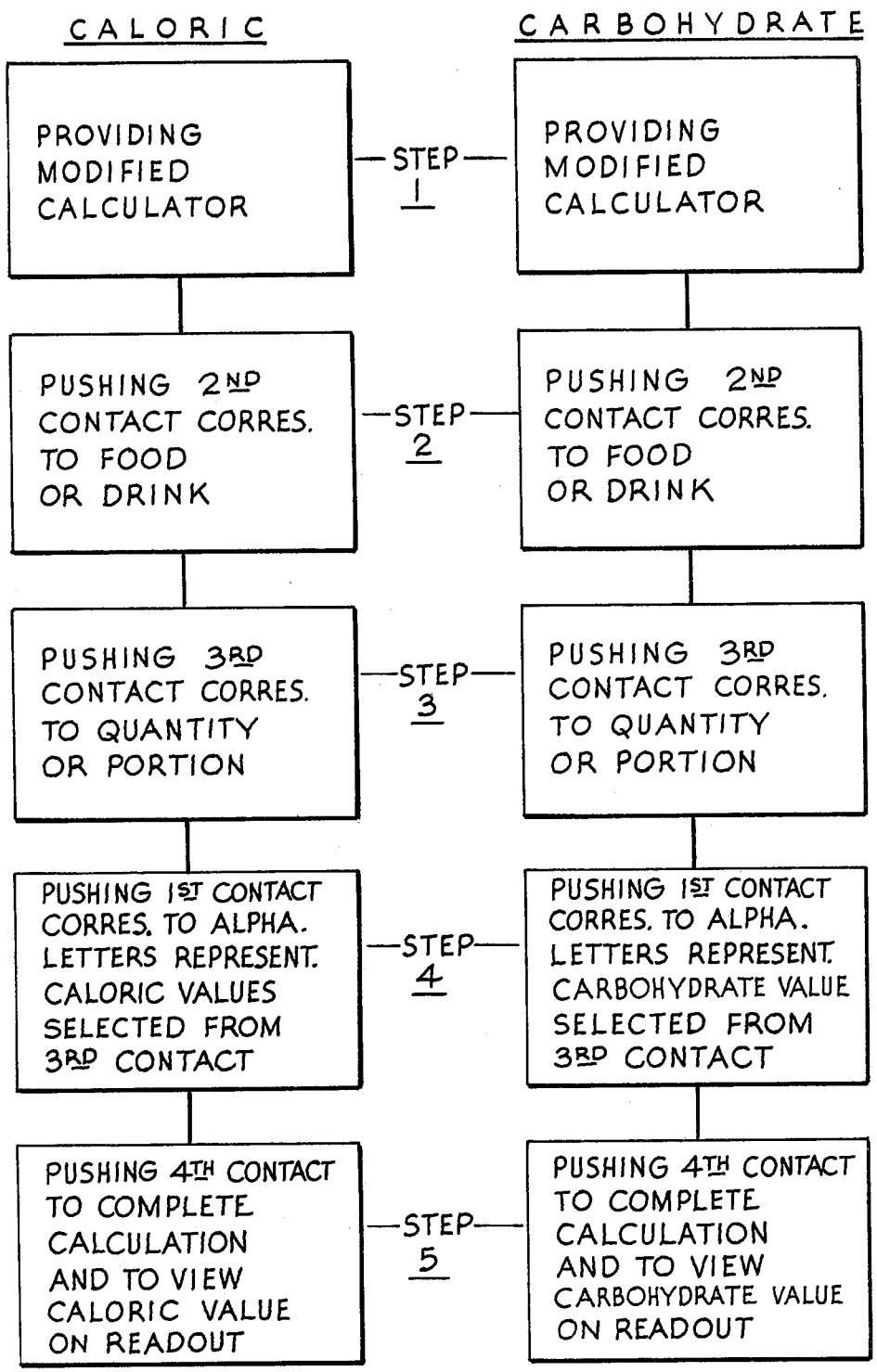
FIG. 5 are block diagrams of the method of the applicant's invention showing the steps in the method hereinafter described.

Referring now to FIG. 5 of the drawing, there is shown in block diagram form the improved method of the applicant's invention which utilizes the before described caloric and/or carbohydrate calculator to determine the respective value of the food and/or drink to be consumed. The left-hand column in FIG. 5 represents the five basic steps of using the applicant's calculator whenever the calculator is designed for determining caloric values while the right-hand column in FIG. 5 represents the five basic steps of using the calculator whenever the calculator is designed for selection of carbohydrate values. It is within the spirit and scope of the invention, and it is to be understood that whenever the calculator is designed for determination of caloric and/or carbohydrate values that the steps shown in FIG. 5 would be operable for both caloric values and carbohydrate values.

It will be understood from a review of FIGS. 1 through 4 of the drawing that basically the applicant utilizes a standard calculator and modifies the keyboard to represent a plurality of first contacts which are comparable to the standard numerical contacts of the standard calculator keyboard but have in place thereof visual indications of alphabetical letters A, B, C, etc. In addition, the modified keyboard contains the second plurality of contacts 18 which visually indicate food and drink items with each food and drink item being given a numerical value. The numerical contacts of the second groups of contacts are connected to the same numerical contacts of the first group of contacts. Since the third group of contacts are all multiplier contacts and since the fourth group of contacts are equals contacts, it should become readily apparent that the use of the calculator becomes one of using it as a standard calculator to multiply numbers together and add the total.

In utilizing the novel calculator herein described, the first step would be to provide the caloric and/or carbohydrate calculator as described. Thereafter the user of the calculator would push a second contact 18 which would correspond to the food or drink item to be selected or consumed and to be calculated by the device. Thereafter the user would push a third contact 20 which would correspond to the quantity or item of food or drink to be consumed and thereafter he would push a first contact 16 corresponding to the alphabetical letter located in proximity to the third contact 20 which he had previously pushed. Thereafter he would push the appropriate fourth contact either 24 or 26 on the calculator that he had to complete the calculation and to view the caloric value on the visual readout 28 of the calculator 10. For example, if the user desired to calculate the caloric value of a glass of vegetable juice, he would first push the second contact 18 which indicates the word "drinks" and would then push the third contact 20 in column 48, shown in FIG. 3 of the drawing. Thereafter he would push the first contact 16 which would indicate the letters "C" and "K" which he would have observed when pushing the third contact 20. Since each second contact 18 has a predetermined numerical value as will be described hereinafter, then it is apparent that actually by selecting a second contact 18 by the word designation "drink", the user is actually pushing a preselected numerical value and multiplying that value by a preindicated value taken from the third contacts 20 to calculate the total caloric and/or carbohydrate value.

The correlation between the visual indications on the first contacts 16 and the numerical value in the calculator circuit would be as follows:

| Visual Letter | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |

| Visual Letter | Numerical Contact |
|---|---|
| L | DECMIAL POINT |

The correlation between the visual item displayed on the second contacts 18 and the numerical value in the electrical circuit is as follows:

| Visual Item | Numerical Contact |
|---|---|
| Drinks | 4 |
| Bread, Cereals | 5 |
| Desserts | 5 |
| Fats, Oils, Dressing | 6 |
| Meats | 6 |
| Milk Products | 4 |
| Snacks | 5 |
| Soups | 8 |
| Vegetable, Fruits | 9 |

From the foregoing it can be seen that the applicant's novel calculator allows a user of the device to quickly select a food or drink item from the second groups of contacts 18 and to then select an appropriate third contact 20 which in turn gives him an alphabetical letter or letters which he then pushes by pushing the appropriate first contact or contacts 16 to complete the calculation. Thereafter by pushing the appropriate fourth contact 24 or 26, the calculated caloric and/or carbohydrate value would be recorded on the digital readout 28 according to which type of calculator was used by the consumer.

Should it be necessary to add a quantity of food and drink items, then the user of the device would depress the fifth contact 30 which is electrically connected to the add circuit of the memory circuit for the standard calculator and after each respective calculation would again press the contact 30. Upon completing his total calculations, he would then depress the contact 32 which is electrically connected to the equals circuit and again would read the entire total caloric and/or carbohydrate value on the digital readout 28. Because of the smaller values used in carbohydrate selection, the contact 58 labeled "L" in the grouping of contacts at the lower portion of the keyboard shown in FIG. 1 of the drawing would be electrically connected to the decimal point circuit of the standard calculator which would allow smaller or fractional values to be calculated. For example, it can be seen by referring to the carbohydrate face-plate shown in FIG. 4 in the column 46 for vegetables and fruits that by pushing the contact 20 in column 48, a visual indication of LJ would be given which would actually represent, when pushing the first group of contacts, the actual designation 0.5 or the value one-half.

It can be seen from the foregoing that the applicant's new and improved calculator has combined a standard numerical four-function calculator with an appropriate caloric and/or carbohydrate value chart to obtain the necessary calculation. By the use of the novel modified calculator keyboard and the respective visual alphabetical indications, there is provided a calculator that achieves many of the objects and advantages of the invention.

Figure 6:
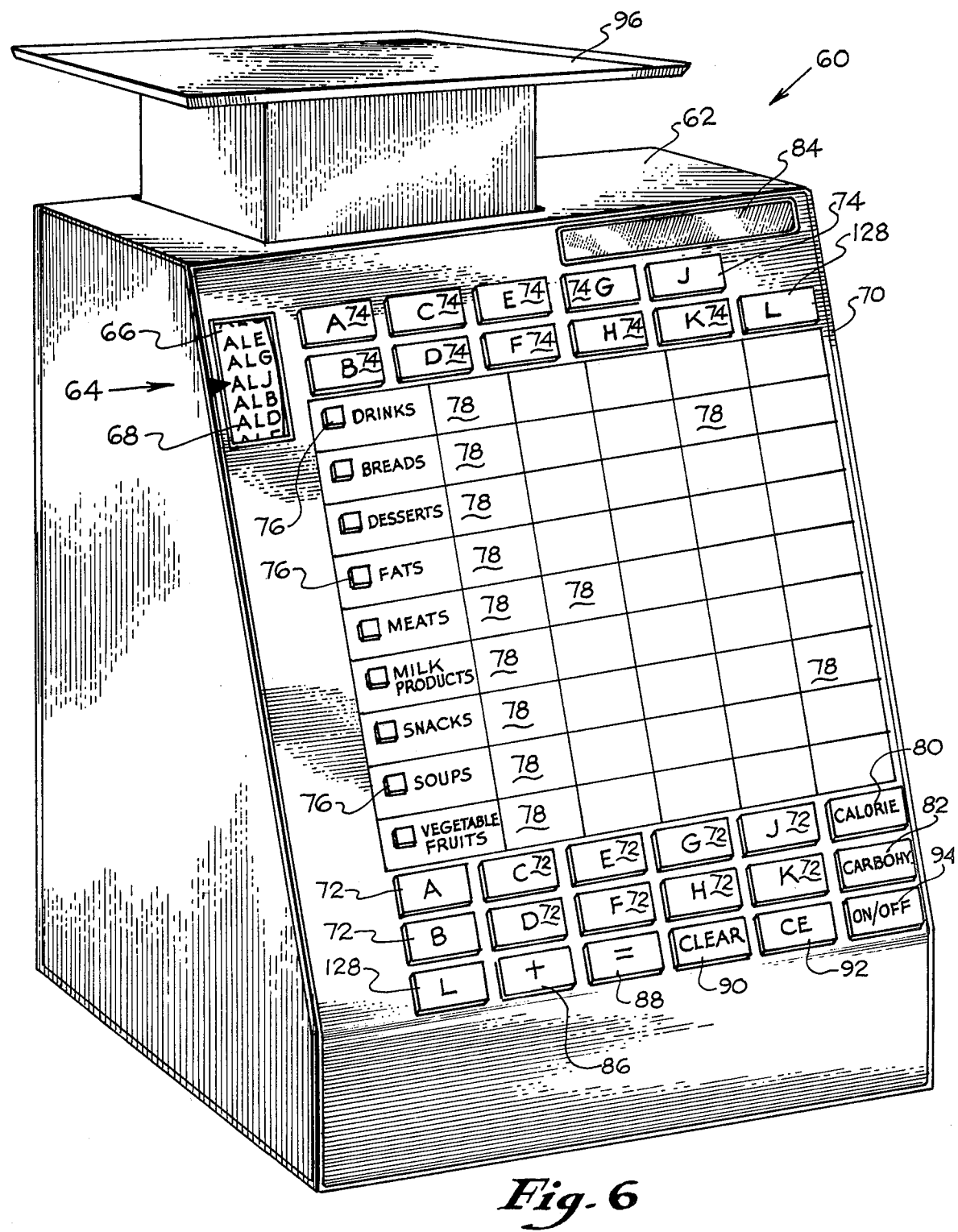
FIG. 6 is a perspective view of a modification of the applicant's basic invention showing the basic invention adapted as modified to be used with a weighing scale case and mechanism of the type used by a housewife or cook.

Referring now to the drawing FIGS. 6-10 in general and in particular to FIG. 6 of the drawings, there is shown a perspective view of a modification of the applicant's new and improved calculator which may be used by a housewife or a cook for calculating a very accurate approximation of the appropriate caloric and/or carbohydrate value of a food or drink item and is shown generally by the numeral 60 which comprises a case 62 having contained therein a standard weight scale shown generally by the numeral 64. The weight scale 64 has a roll dial indicator 66 containing indications 68 of varying combinations of alphabetical letters. The function of the weight scale 64 and roll dial indicator 66 in the modified calculator shown in FIGS. 6-10 will be described more fully hereinafter and especially when referring to FIG. 7 of the drawings.

Case 62 also contains a standard numerical calculator electrical operation circuit of the type having the usual four-basic-functions of addition, subtraction, multiplication and division and which has been modified further from the modification herein-described before when referring to the basic invention. Typical calculators of this type would be the calculator manufactured by Texas Instrument Co. No. TI-1680, No. TI-30SP, No. TI-1025, No. TI-1000 and other similar calculators manufactured by the same company and also by other companies of the type readily available in the marketplace today.

The applicant's modified calculator utilized in combination with the weighing scale as shown in FIGS. 6-10 of the drawings contains a modified calculator keyboard 70 which has a plurality of first contacts 72 which are numerical in function as will be described hereinafter and indicate visually alphabetical letters as shown in FIG. 6. A plurality of second contacts 74 are numerical in function and indicate visually alphabetical letters corresponding to the alphabetical indications 68 indicated on the exposed roll dial indicator 66. A plurality of third contacts 76 are multiplier contacts and have located in proximity thereto indications of predetermined alphabetical letters corresponding to caloric and/or carbohydrate values of food and drink items. In the embodiment shown in FIG. 6 of the drawing a single vertical row of third contacts 76 would be provided at the left-hand side of the calculator and each individual third contact would have located beside it visual indications of various food and drink items with the predetermined alphabetical letters corresponding to caloric and/or carbohydrate values of food and drink items being juxtapositioned immediately to the right thereof especially as shown in FIGS. 8 and 9 of the drawings. In FIG. 6 of the drawing the indications are shown by the numeral 78 and for a further clarification of the indications, reference will be made to FIGS. 8 and 9 of the drawings to be described hereinafter to show specifically the various food and drink catagories and indications of the food and drink items as well as the predetermined alphabetical letters.

In the calculator shown in FIG. 6 of the drawings, the plurality of second contacts indicating alphabetical letters total eleven letters and the plurality of third contacts indicating food and drink categories total nine in the embodiment shown. It is within the spirit and scope of the invention that the total number of first, second, third and fourth contacts will vary according to the design of the manufacturer of the calculator and the applicant is not to be limited to the exact number shown in the drawings.

In the calculator shown in FIG. 6, there is also provided a fourth contact 80 and a fourth contact 82 with the fourth contact 80 indicating the wording calorie while the fourth contact 82 indicates the word carbohydrates. The plurality of fourth contact 80 and 82 are equal contacts in the electrical circuit as will be described hereinafter and will function in the manner to be described. The applicant's calculator also contains a standard numerical read-out 84 of the type containing a plurality of visual digital numbers which are illuminated from the standard electrical circuit by means of a self-contained battery positioned within the calculator case 62 or by means of solar cells also positioned in the case 62 in a manner to collect natural or artificial light.

A fifth contact 86 is positioned on the keyboard and indicates a "+" while another fifth contact 88 is positioned on the keyboard and indicates an "=" with the "+" contact 86 being electrically connected to the memory add circuit of the standard numerical calculator as will be hereinafter described and the "=" contact 88 being electrically connected to the "=" circuit of the standard numerical calculator as will also be hereinafter described.

Completing the keyboard of the applicant's modified calculator as shown in FIGS. 6-10 of the drawings would be a standard contact 90 indicating "clear" and a standard contact 92 indicating a "CE" with these two contacts functioning in the standard way to clear any errors or to clear the entire keyboard as is used in the standard calculator circuit. An on-and-off contact 94 is also provided on the applicant's calculator keyboard to turn the calculator on and to turn it off as desired by the user of the device.

Figure 7:
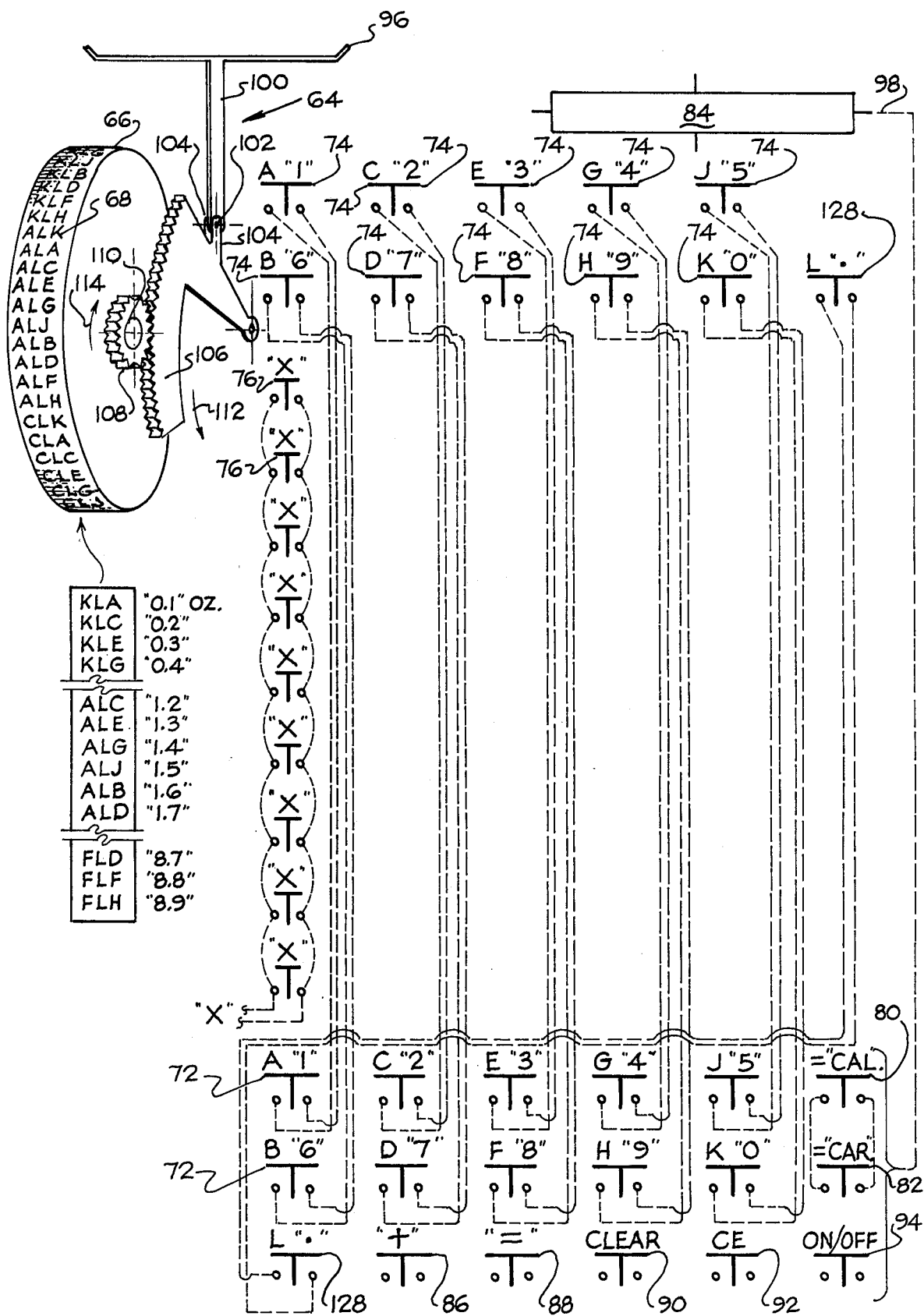
FIG. 7 is a schematic view of the modified calculator of the applicant's basic invention as shown in FIG. 6.

The applicant's modified calculator as shown in FIGS. 6-10 of the drawing also utilizes a weighing platform 96 which is physically connected to the weight scale 64 and roll dial indicator 66 as will be described hereinafter when referring to FIG. 7 of the drawing. In utilization of the calculator shown in FIGS. 6-10 of the drawing, a pre-selected food and/or drink item is placed on the weighing platform 96 to give a visual alphabetical indication in the weight scale 64 which will be utilized as hereinafter described by the user of the device.

Referring now to FIG. 7 of the drawing, there is shown a schematic view of the electrical contacts of the various contacts hereinbefore described and showing how they would be electrically connected to each other in order to function in the manner hereinafter described. The various contacts are positioned on the modified calculator keyboard as shown in FIG. 6 of the drawing and there is indicated above each contact, the numerical number or function of that particular contact in operation of the calculator. It can be seen, for example, that the first contacts 72 are the standard numerical contacts of the standard numerical calculator circuitry and number from 0 to 9 including a decimal point as is common in the calculators beforementioned. There is also shown a letter beside each numerical value of the first contacts 72 which would correspond to the letter that would be actually indicated on the contact key as shown in FIG. 6 of the drawing.

The plurality of second contacts 74 are numerical in function and the numerical value of each second contact 74 is indicated in FIG. 7 of the drawing positioned on the respective second contact. It can be seen that the actual keyboard indication on the second contact would be as shown in FIG. 6 of the drawing with the respective keys indicating alphabetical letters and not the numerical value.

Each third contact 76 is a multiplier contact as indicated by the small "×" positioned above the contact in FIG. 7 of the drawing and is electrically connected in parallel to each other and to the multiplier circuit of the standard numerical keyboard. It will also be seen by referring to FIG. 7 of the of the drawing that each of the numerical second contacts 74 would be electrically connected in parallel to the similar first numerical contact in the standard numerical calculator circuit. While it is not shown on the schematic, it is to be understood that the connection of the plurality of first electrical contacts 72 as well as the contacts 80, 82, 86, 88, 90, 92 and 94 would be electrically connected to their counterpart in the standard numerical calculator circuit. It can also be seen that the contact 80 which would indicate the word, calorie, as shown in FIG. 6 of the drawing would be an equal contact while the contact 82, which would indicate the word, carbohydrate, would also be an equal contact, and these two contacts would be connected to their counterparts in the standard numerical circuit.

The digital read-out 84 would also be connected by means of line or lines 98 to the respective calculator circuitry thus completing the total circuitry for the modified keyboard as shown in FIGS. 6–10 of the drawing and as used in the applicant's modified calculator.

By referring to the weight scale unit 64 as shown in FIG. 7 of the drawing it can be seen how the weighing platform 96 is connected to the roll dial indicator 66 by means of the rod 100 which is connected to the pin 102 and to a pair of arms 104 contained on the segmental gear 106. The roll dial indicator 66 also contains a gear 108 centrally located on a pin 110 which is driven by the segmental gear 106. When formed thusly and when a portion of food and/or drink is placed on the weighing platform 96, the segmental gear 106 will travel in the direction shown by the arrow 112 causing the gear 108 to rotate in the direction shown by the arrow 114 to give a visual alphabetical indication on the weight scale indicator 64 as shown in FIG. 6 of the drawing.

The correlation between the visual indications on the roll dial indicator 66 and the numerical value in ounces is as follows:

| Visual Letter | Ounces | Visual Letter | Ounces |
|---|---|---|---|
| KLA | 0.1 | KLD | 0.7 |
| KLC | 0.2 | KLF | 0.8 |
| KLE | 0.3 | KLH | 0.9 |
| KLG | 0.4 | ALK | 1.0 |
| KLJ | 0.5 | ALA | 1.1 |
| KLB | 0.6 | ALC | 1.2 |
| ALE | 1.3 | JLC | 5.2 |
| ALG | 1.4 | JLE | 5.3 |
| ALJ | 1.5 | JLG | 5.4 |
| ALB | 1.6 | JLJ | 5.5 |
| ALD | 1.7 | JLB | 5.6 |
| ALF | 1.8 | JLD | 5.7 |
| ALH | 1.9 | JLF | 5.8 |
| CLK | 2.0 | JLH | 5.9 |
| CLA | 2.1 | BLK | 6.0 |
| CLC | 2.2 | BLA | 6.1 |
| CLE | 2.3 | BLC | 6.2 |
| CLG | 2.4 | BLE | 6.3 |
| CLJ | 2.5 | BLG | 6.4 |
| CLB | 2.6 | BLJ | 6.5 |
| CLD | 2.7 | BLB | 6.6 |
| CLF | 2.8 | BLD | 6.7 |
| CLH | 2.9 | BLF | 6.8 |
| ELK | 3.0 | BLH | 6.9 |
| ELA | 3.1 | DLK | 7.0 |
| ELC | 3.2 | DLA | 7.1 |
| ELE | 3.3 | DLC | 7.2 |
| ELG | 3.4 | DLE | 7.3 |
| ELJ | 3.5 | DLG | 7.4 |
| ELB | 3.6 | DLJ | 7.5 |
| ELD | 3.7 | DLB | 7.6 |

-continued

| Visual Letter | Ounces | Visual Letter | Ounces |
|---|---|---|---|
| ELF | 3.8 | DLD | 7.7 |
| ELH | 3.9 | DLF | 7.8 |
| GLK | 4.0 | DLH | 7.9 |
| GLA | 4.1 | FLK | 8.0 |
| GLC | 4.2 | FLA | 8.1 |
| GLE | 4.3 | FLC | 8.2 |
| GLG | 4.4 | FLE | 8.3 |
| GLJ | 4.5 | FLG | 8.4 |
| GLB | 4.6 | FLJ | 8.5 |
| GLD | 4.7 | FLB | 8.6 |
| GLF | 4.8 | FLD | 8.7 |
| GLH | 4.9 | FLF | 8.8 |
| JLK | 5.0 | FLH | 8.9 |
| JLA | 5.1 | | |

By referring to FIGS. 6 and 7 together as well as the hereinbefore described materials relating to those Figures, it should be apparent that the applicant's modified calculator basically uses the functions of the standard weight scale and the standard modified calculator, with a totally modified keyboard having visual indications of food and drink items and visual indications of alphabetical letters in combination with a plurality of multiplier keys having visual indications contained either thereon or beside the respective multiplier key. Before describing the operation of the applicant's calculator, reference should now be made to FIG. 8 of the drawing which would represent the face plate of the applicant's keyboard in the area of the plurality of third contacts 76 whenever a calculator was constructed which would be designed for use to calculate calories only. In a similar manner, the drawing shown in FIG. 9 would represent the face plate of a calculator which would be designed to be used as a calculator for figuring carbohydrates only. When it would be desirous to manufacture a calculator capable of calculating both calories and carbohydrates, it is within the spirit and scope of the invention that the face plate of the keyboard surrounding the contacts 76 would be a combination of the face plate shown in FIGS. 8 and 9 of the drawing.

It can be seen by referring to both FIGS. 8 and 9 that there is provided in the face plate a left-hand vertical column 116 having indications of various food and drink catagories. Each food and drink mentioned in column 116 would be in proximity to contact 76 and would then be related horizontally to the appropriate specific item which would be printed on the face plate and would have an appropriate alphabetical letter or letters printed in proximity to each item. For example, when referring to column 116 of FIG. 8 which would show the caloric face plate, it will be seen that there are listed three (3) common drinks available to the user. These drinks would be vegetable juice, fruit juice and table wine, and there would be indicated the alphabetical letters in proximity to each item. For example the vegetable juice would have indicated the alphabetical letter "E" while the fruit juice would have the alphabetical letters indicated "AE" and the table wine would have the alphabetical letter indicated "G". Immediately to the right of this would be represented a drink item of a jigger of 80 proof whiskey with the alphabetical indication in proximity to this item of "DB". In a like manner, other food and drink items are indicated in the various columns and opposite each item would be indicated an alphabetical designation which would be hereinafter in describing the operation of the calculator.

When manufacturing the face plate and positioning the various food and drink items on the face plate, it may be desirous to group the food and drink items in such a manner that the lower caloric or carbohydrate items would be all positioned vertically in one column with the next higher caloric or carbohydrate values being positioned next to them. For example, the lower caloric and carbohydrate values may all be positioned in the vertical column 118 while the next higher caloric and carbohydrate values would be positioned in the column 120 with the column 122, 124 and 126 each representing higher caloric and carbohydrate values. It may also be desirous to color-code the respective vertical columns 118-126 in such a manner to visually indicate to the user of the device that the items in that particular column have either a high or a low caloric or carbohydrate value or some intermediate value therebetween. For example, it may be desirous to color-code the vertical column 118 in a dark green to indicate a low caloric or carbohydrate value while the vertical column 120 would be color-coded in a light green and the vertical column 122 would be color-coded yellow. In a like manner the vertical column 124 would be color-coded light red and the vertical column 126 would be color-coded red to indicate the highest caloric carbohydrate value of the items being chosen. In this manner it can be seen by the use of the color-coding, the user of the device can instantly see when he is selecting and calculating a higher food value and he may want to re-evaluate his selection to a lower caloric or carbohydrate value.

Figure 10:
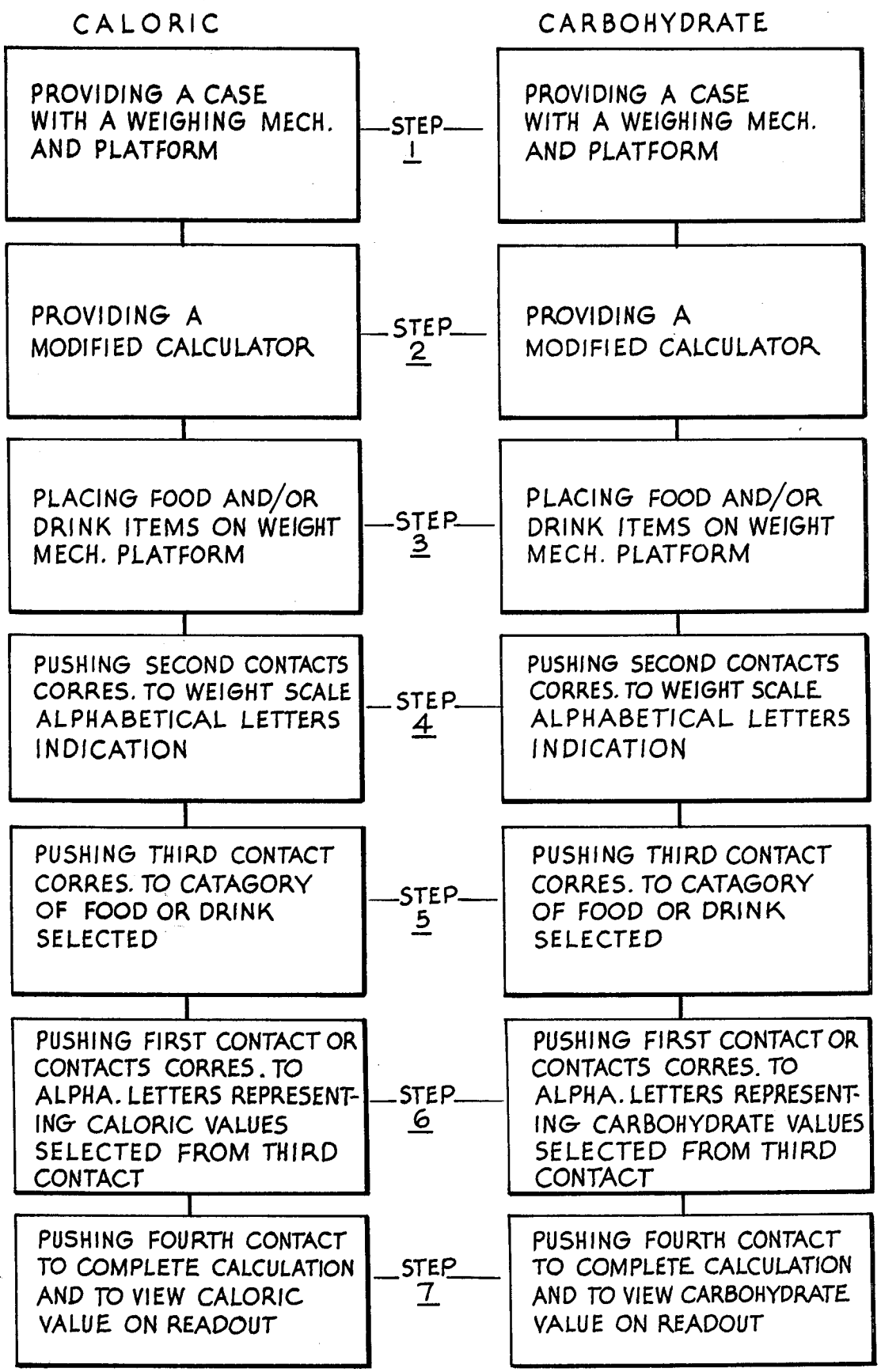
FIG. 10 are block diagrams of the method using the applicant's modified calculator shown in FIG. 6.

Referring now to FIG. 10 of the drawing, there is shown in block diagram form the improved method of the applicant's modified invention which utilizes the before-described caloric and/or carbohydrate calculator to determine the respective value of the food and/or drink to be consumed. The left-hand column of FIG. 10 represents the seven basic steps of using the applicant's calculator whenever the calculator is designed for determining caloric values while the right-hand column in FIG. 10 represents the seven basic steps of using the calculator whenever the calculator is designed for selection of carbohydrate values. It is within the spirit and scope of the invention, and it is to be understood that whenever the calculator is designed for determination of caloric and/or carbohydrate values that the steps shown in FIG. 10 would be operable for both caloric values and carbohydrate values.

It will be understood from a review of FIGS. 6 through 9 of the drawings that basically the applicant in the modification shown utilizes a standard weight scale with the dial indicator modified to show alphabetical letters which are comparable to the standard numerical scale. In addition there is utilized a standard calculator which is modified in the keyboard to represent a plurality of first contacts which are comparable to the standard numerical contacts of the standard calculator keyboard but have in place thereof visual indications of alphabetical letters A, B, C, etc. In addition, the modified keyboard contains the second plurality of contacts 74 which also visually indicate alphabetical letters. The numerical contacts of the second groups of contacts are connected to the same numerical contacts of the first group of contacts. Since the third group of contacts 76 are all multiplier contacts and since the fourth group of contacts 80 and 82 are "equals" contacts, it should become readily apparent that the use of the calculator becomes one of using it as a standard calculator to multiply numbers together and add the total.

In utilizing the novel modified calculator as shown in FIGS. 6-10, the first step would be to provide a case with a weighing mechanism contained therein and which would have an exposed dial indicating varying combinations of alphabetical letters with the mechanism further having a weighing platform positioned on the exterior of the case. Thereafter there would be provided a caloric calculator within the case and with the calculator having a visual read-out and which would comprise a modified standard numerical circuitry having a plurality of first, second and third groups of contacts and at least a fourth contact. Thereafter the user of the device would place a predetermined amount of food or drink item on the platform and would read a combination of alphabetical letters on the weighing mechanism. Thereafter he would push a group of second contacts corresponding to the weight scale indication of combinations of various alphabetical letters and would thereafter push a third contact corresponding to the category of food or drink being weighed. Completing this he would push a first contact or contacts corresponding to the alphabetical letter of the exact food and drink item being weighed shown located in proximity to the third contact previously pushed and he would push the fourth to complete the calculation and to view the caloric value on the visual read-out of the calculator. It can be seen that since each second contact 74 has a predetermined numerical value as will be described hereinafter, then it is apparent that actually by selecting a second contact 74 by the alphabetical designation shown on the scale indicator, the user is actually pushing a numerical value and multiplying that value by a pre-indicated value taken from the third contacts 76 to calculate the total caloric and/or carbohydrate value. In utilizing the modified calculator to provide carbohydrate units, the same basic steps in the method would be utilized as described in regard to the caloric calculator.

The correlation between the visual indications on the first contacts and the numerical value in the calculator circuit would be as follows:

| Visual Letter | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |
| L | DECMIAL POINT |

The correlation between the visual items displayed on the second contacts 74 and the numerical value in the electrical circuit is as follows:

| Visual Item | Numerical Contact |
|---|---|
| A | 1 |
| B | 6 |
| C | 2 |
| D | 7 |
| E | 3 |
| F | 8 |
| G | 4 |
| H | 9 |

-continued

| Visual Item | Numerical Contact |
|---|---|
| J | 5 |
| K | 0 |
| L | DECIMAL POINT |

From the foregoing it can be seen that the applicant's novel modified calculator as shown in FIGS. 6-10 of the drawing allows the user of the device to weigh a food and/or drink item and to quickly select the alphabetical weight indication and to then select an appropriate third contact 76 which in turn gives the user an alphabetical letter or letters which he then pushed by pushing the appropriate first contact or contacts 72 to complete the calculation. Thereafter by pushing the appropriate fourth contacts 80 or 82, the calculated caloric and/or carbohydrate value would be recorded on the digital read-out 84 according to which type of calculator was used by the consumer.

Should it be necessary to add a quantity of food and drink items, then the user of the device would depress the fifth contact 86 which is electrically connected to the add circuit of the memory circuit for the standard modified calculator and after each respective calculation would again press the contact 86. Upon completing his total calculations, he would then depress the contact 88 which is electrically connected to the equal circuit and would again read the entire total caloric and/or carbohydrate value on the digital read-out 84. The contact labeled "L" and shown by the numeral 128 in the grouping of contacts 72 and 74 of the keyboard shown in FIG. 6 of the drawings would be electrically connected to the decimal point circuit of the standard calculator which would allow smaller or fractional values to be calculated.

It can be seen from the foregoing that the applicant's modified calculator has combined a standard numerical four-function calculator with an appropriate caloric and/or carbohydrate chart in combination with a weighing scale and mechanism to obtain the necessary calculation. By the use of the novel modified calculator keyboard and the respective visual alphabetical indications, there is provided a calculator that achieves all the objects and advantages of the invention.

Nevertheless, it should become apparent from a review of the drawings and from a reading of the specification that many changes may be made in the parts and the applicant's invention is not to be limited to the exact embodiment shown which has been shown by way of illustration only.

Having described my invention, I claim:
1. A caloric and carbohydrate calculator, comprising:
   (a) a calculator case;
   (b) a standard numerical calculator electrical operation circuit contained within the case and the standard circuit containing at least a memory add circuit and an equal circuit, as well as other circuits and contacts;
   (c) a modified calculator keyboard having a plurality of first, second, third and fourth groups of contacts and whereby;
   (1) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;
   (2) the plurality of second contacts are numerical in function and indicate pre-determined food and drink items and are electrically connected to the calculator electrical circuit in such a manner that each second contact has a predetermined numerical value and each second contact is electrically connected in parallel to other similar second numerical contacts and to the similar first numerical contact in the standard numerical calculator;
   (3) the plurality of third contacts are multiplier contacts and have located in proximity thereto indications of predetermined alphabetical letters corresponding to caloric and carbohydrate values of varying portions of food and drink items, the third contacts being electrically connected together and to the standard calculator circuit multiplier contact;
   (4) the plurality of fourth contacts are equal contacts in the electrical circuit and indicate the wording calories and carbohydrates; and
   (d) a standard numerical readout positioned in the calculator case and electrically connected to the circuit.

2. The calculator as defined in claim 1 wherein the first contacts have visual alphabetical letters and are electrically connected to the calculator circuit as folows:

| Visual Letter | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |
| L | DECMIAL POINT |

3. The calculator as defined in claim 1 wherein the second contacts indicate food and drink items and are electrically connected to the calculator circuit as follows:

| Visual Item | Numerical Contact |
|---|---|
| Drinks | 4 |
| Bread, Cereals | 5 |
| Desserts | 5 |
| Fats, Oils, Dressing | 6 |
| Meats | 6 |
| Milk Products | 4 |
| Snacks | 5 |
| Soups | 8 |
| Vegetable, Fruits | 9 |

4. The calculator as defined in claim 1 wherein the third contacts indicate alphabetical letters corresponding to caloric and carbohydrate values of varying portions and/or types of food and drink items as follows:
   (a) Drinks

| Calorie Portion or Type | Calorie Letter Indication | Carbohydrate Portion or type | Carbohydrate Letter Indication |
|---|---|---|---|
| Veg. Juice | CK | Jigger 80 Proof Whiskey | K |
| Fruit Juice | CK | Wine Glass | |
| Table Wine | CK | Table Wine | A |
| Jigger 80 Proof Whiskey | CJ | Dessert Wine Fruit Flavor Drinks | E |
| Ginger Ale | EA | Cola | J |
| Dessert Wine | EA | Beer | J |
| Cola | EF | Root Beer | J |
| Beer | EF | Ginger Ale | J |
| Root Beer | EF | Cider | D |
| Fruit Flavors | GE | Lemonade | D |

(b) Breads and Cereals

| Calorie Portion or Type | Calorie Letter Indication | Carbohydrate Portion or Type | Carbohydrate Letter Indication |
|---|---|---|---|
| Pretzel | D | Pretzel | A |
| Cracker | D | Cracker | A |
| Slice Bread | AJ | Pancake | C |
| Pancake | AJ | Slice Bread | E |
| Corn or Rice Cereals | CK | Cereals | E |
| | | Bran Cereal | G |
| Grits | CK | | |
| | | Biscuit | G |
| Roll | EK | | |
| | | Roll | G |
| Biscuit | EK | | |
| | | Rice | B |
| Rice | EK | | |
| | | Spaghetti & | |
| Wheat Cereal | EK | Meatballs | B |
| Pizza | GK | Waffe | B |
| Spaghetti & Meatballs | GK | | |
| Waffle | GK | | |

(c) Desserts and Sweets

| Calorie Portion or Type | Calorie Letter Indication | Carbohydrate Portion or Type | Carbohydrate Letter Indication |
|---|---|---|---|
| Hard Candy | CK | Hard Candy | C |
| Angel Cake | CK | Cookie | C |
| Sirup | CK | Fig Bar | E |
| Jellies | CK | Custard | E |
| Fig Bar | CK | Sirup | E |
| Fruit Cake | EK | Jelly | E |
| Cookie | EK | Ice Cream | J |
| Custard | EK | Angel Cake | B |
| Ice Cream | EK | Sherbet | B |
| Ginger Bread | GK | Candy Bar | F |
| Plain Cake with icing | GK | Pie | F |
| Pie | BK | | |
| Pecan Pie | FK | | |
| Candy Bar | FK | | |

(d) Fats, Oils and Dressings

| Calorie Portion or Type | Calorie Letter Indication | Carbohydrate Portion or Type | Carbohydrate Letter Indication |
|---|---|---|---|
| Lo-Cal Dressing | G | Mayonnaise | K |
| Home Cooked | | 1 Pat Butter | K |
| Salad Dressing | F | | |
| | | Salad Oil | K |
| Pat Butter | F | | |
| | | Salad Dressing | LJ |
| Salad Dressing | AE | | |
| | | Gravy | LJ |
| Gravy | AE | | |
| | | Peanut Butter | LJ |
| Mayonnaise | AD | | |
| Peanut Butter | AD | | |
| Salad Oil | CA | | |

(e) Meats

| Calorie Portion or Type | Calorie Letter Indication | Carbohydrate Portion or Type | Carbohydrate Letter Indication |
|---|---|---|---|
| Egg | AD | Can Fish | K |
| Bacon | AD | Fowl | K |
| Clam | AD | Lunch Meat | K |
| Oyster | AD | Corn Beef | K |
| Nuts | AD | Boil Egg | K |
| Lunch Meat | AD | Steak/Chops | K |
| Shrimp | CJ | Clam | LJ |
| Broiled Fish | CJ | Egg Omelet | LJ |
| Meatloaf | CJ | Bacon | LJ |
| Corned Beef | CJ | Meatloaf | LJ |
| Beef Stew | EG | Sausage | LJ |
| Sausage | EG | Shrimp | A |
| Broiled Turkey, Chicken | EG | Fried Fish | A |
| | | Oyster | C |
| Fried Fish | EG | | |
| | | Nuts | C |
| Liver | GC | | |
| | | Liver | C |
| Chili | GC | | |
| | | Chili | C |
| Ham | GC | | |
| | | Beef Stew | C |
| Veal Cutlut | GC | | |
| | | Dried Beans | G |
| Lean Meats | GC | | |
| | | Pot Pies | G |
| Meat with Fat | JF | | |
| Steak/Chops | JF | | |
| Pot Pies | JF | | |

(f) Milk Products

| Calorie Portion or Type | Calorie Letter Indication | Carbohydrate Porton or Type | Carbohydrate Letter Indication |
|---|---|---|---|
| Buttermilk | CJ | Slice Cheese | LC |
| Skim Milk | CJ | Sour Cream | LC |
| Slice Cheese | CJ | Skim | C |
| Yoghurt | EF | Buttermilk | E |
| Custard | EF | Whole | E |
| Sherbet | EF | Condensed | E |
| Evaporated | JK | Chocolate | J |
| Whole | JK | Sherbet | B |
| Chocolate Flavor | JK | Malt | B |
| Sour Cream | BE | Shake | B |
| Cocoa | BE | | |
| Chocolate Soda | BE | | |
| Malt | FD | | |
| Chocolate Shake | FD | | |

(g) Snacks

| Calorie Portion or Type | Calorie Letter Indication | Carbohydrate Portion or Type | Carbohydrate Letter Indication |
|---|---|---|---|
| Olives | AK | Pickle | A |
| Pickles | AK | Olives | A |
| Popcorn | AK | Popcorn | C |
| Potato Chips | CK | Potato Chips | E |
| French Fries | EK | French Fries | G |
| Corn Chips | EK | Corn Chips | G |
| Pizza Slice | CK | Pizza | J |
| Donut | CK | Donut | J |
| Hot Dog | JK | Hot Dog | J |
| Hamburger | JK | Hamburger | J |

(h) Soups

| Calorie Portion or Type | Calorie Letter Indication | Carbohydrate Portion or Type | Carbohydrate Letter Indication |
|---|---|---|---|
| Broth | B | Bouillion | K |
| Chicken with Rice and Noodle | B | Broth | LJ |
| | | Chicken with Rice | A |
| Vegetable | H | Beef Noodle | A |
| Beef Noodle | H | Mushroom | A |
| Tomato | H | Clam Chowder | C |
| Clam Chowder | H | Tomato | C |
| Asparagus | AE | Vegetable | C |
| Minestrone | AE | Bean | E |
| Vegetable with Beef | AE | | |
| | | Pea | E |
| Mushroom | AH | | |
| Split Pea | AH | | |
| Tomato Milk | CJ | | |
| Bean with Pork | CJ | | |
| Oyster Stew | CJ | | |

(i) Vegetables and Fruits

| Calorie Portion or Type | Calorie Letter Indication | Carbohydrate Portion or Type | Carbohydrate Letter Indication |
|---|---|---|---|
| Cooked Green Beans | E | Raw Vegetables Cooked | LJ |
| Raw Vegetables | E | Green Beans | LJ |
| Boiled Vegetables | B | Cooked Greens | A |
| Raw Fruit | AC | Raw Fruit | C |
| Baked Potato | AC | Cooked Vegetables | C |
| Dried Beans | AC | Cooked Fruit | E |
| Corn on Cob | AC | Dried Beans | E |
| Cooked Fruit | AD | Pre-Sweet Cooked Fruit | G |
| French Fries | AD | | |
| | | Sweet Potato | G |
| Sweet Potatoe | AD | | |
| Date | CE | | |
| Raisin | CE | | |
| Avacodos | CD | | |
| Pre-Sweet Cooked Fruits | CE | | |

5. The calculator as defined in claim 1 further comprising a plurality of fifth groups of contacts and whereby at least one of the fifth contacts indicates a plus and is electrically connected to the memory add circuit of the standard numerical calculator and at least one of the fifth contacts indicates an equal and is electrically connected to the equal circuit of the standard numerical calculator.

6. In a calculator of the type wherein a standard numerical electrical operative circuit is contained within a case, the circuit containing at least a memory add circuit and an equal circuit as well as other circuits and contacts, and has a plurality of pushbutton keys on the keyboard connected to a numerical readout so that a plurality of calculations, such as adding, subtracting, dividing and multiplying, may be made by pushing the appropriate pushbutton, the improvement comprising modifying the calculator keyboard and electrical circuit by providing a plurality of first, second and third groups of contacts and at least one fourth contact, whereby, (a) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;

(b) the plurality of second contacts are numerical in function and indicate pre-determined food and drink items and are electrically connected to the calculator electrical circuit in such a manner that each second contact has a pre-determined numerical value and each second contact is electrically connected in parallel to other similar second numerical contacts and to the similar first numerical contact in the standard numerical calculator;

(c) the plurality of third contacts are multiplier contacts and have located in proximity thereto indications of predetermined alphabetical letters corresponding to caloric values of varying portions of food and drink items, the third contacts being electrically connected together and to the standard calculator circuit multiplier contact; and (d) the fourth contact is an equal contact in the electrical circuit and indicates the wording "calorie".

7. The improvement as defined in claim 6 wherein the first contacts have visual alphabetical letters and are electrically connected to the calculator circuit as follows:

| Visual Letter | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |
| L | DECMIAL POINT |

8. The improvement as defined in claim 6 wherein the second contacts indicate food and drink items and are electrically connected to the calculator circuit as follows:

| Visual Item | Numerical Contact |
|---|---|
| Drinks | 4 |
| Bread, Cereals | 5 |
| Desserts | 5 |
| Fats, Oils, Dressing | 6 |
| Meats | 6 |
| Milk Products | 4 |
| Snacks | 5 |
| Soups | 8 |

| Visual Item | Numerical Contact |
|---|---|
| Vegetable, Fruits | 9 |

9. The improvement as defined in claim 6 wherein the third contacts indicate alphabetical letters corresponding to caloric values of varying portions and/or types of food and drink items as follows:

(a) Drinks

| Calorie Portion or Type | Calorie Letter Indication |
|---|---|
| Veg. Juice | CK |
| Fruit Juice | CK |
| Table Wine | CK |
| Jigger 80 Proof Whiskey | CJ |
| Ginger Ale | EA |
| Dessert Wine | EA |
| Cola | EF |
| Beer | EF |
| Root Beer | EF |
| Fruit Flavors | GE |

(b) Breads and Cereals

| Calorie Portion or Type | Calorie Letter Indication |
|---|---|
| Pretzel | D |
| Cracker | D |
| Slice Bread | AJ |
| Pancake | AJ |
| Corn or Rice Cereals | CK |
| Grits | CK |
| Roll | EK |
| Biscuit | EK |
| Rice | EK |
| Wheat Cereal | EK |
| Pizza | GK |
| Spaghetti & Meatballs | GK |
| Waffle | GK |

(c) Desserts and Sweets

| Calorie Portion or Type | Calorie Letter Indication |
|---|---|
| Hard Candy | CK |
| Angel Cake | CK |
| Sirup | CK |
| Jellies | CK |
| Fig Bar | CK |
| Fruit Cake | EK |
| Cookie | EK |
| Custard | EK |
| Ice Cream | EK |
| Giner Bread | GK |
| Plain Cake with icing | GK |
| Pie | BK |
| Pecan Pie | FK |
| Candy Bar | FK |

(d) Fats, Oils and Dressings

| Caloric Portion or Type | Calorie Letter Indication |
|---|---|
| Lo-Cal Dressing Home Cooked Salad Dressing | G |
| Pat Butter | F |
| Salad Dressing | F |
| Gravy | AE |
| Mayonnaise | AE |
| Peanut Butter | AD |
| Salad Oil | AD |
|  | CA |

(e) Meats

| Calorie Portion or Type | Calorie Letter Indication |
|---|---|
| Egg | AD |
| Bacon | AD |
| Clam | AD |
| Oyster | AD |
| Nuts | AD |
| Lunch Meat | AD |
| Shrimp | CJ |
| Broiled Fish | CJ |
| Meatloaf | CJ |
| Corned Beef | CJ |
| Beef Stew | EG |
| Sausage | EG |
| Broiled Turkey, Chicken | EG |
| Fried Fish | EG |
| Liver | GC |
| Chili | GC |
| Ham | GC |
| Veal Cutlet | GC |
| Lean Meats | GC |
| Meat with Fat | JF |
| Steaks/Chops | JF |
| Pot Pies | JF |

(f) Milk Products

| Calorie Portion or Type | Calorie Letter Indication |
|---|---|
| Buttermilk | CJ |
| Skim Milk | CJ |
| Slice Cheese | CJ |
| Yoghurt | EF |
| Custard | EF |
| Sherbet | EF |
| Evaporated | JK |
| Whole | JK |
| Chocolate Flavor | JK |
| Sour Cream | BE |
| Cocoa | BE |
| Chocolate Soda | BE |
| Malt | FD |
| Chocolate Shake | FD |

(g) Snacks

| Calorie Portion or Type | Calorie Letter Indication |
|---|---|
| Olives | AK |
| Pickles | AK |
| Popcorn | AK |
| Potato Chips | CK |
| French Fries | EK |
| Corn Chips | EK |

-continued

| Calorie Portion or Type | Calorie Letter Indication |
|---|---|
| Pizza Slice | CK |
| Donut | CK |
| Hot Dog | JK |
| Hamburger | JK |

(h) Soups

| Calorie Portion or Type | Calorie Letter Indication |
|---|---|
| Broth | B |
| Chicken with Rice or Noodle | B |
| Vegetable | H |
| Beef Noodle | H |
| Tomato | H |
| Clam Chowder | H |
| Asparagus | AE |
| Minestrone | AE |
| Vegetable with Beef | AE |
| Mushroom | AH |
| Split Pea | AH |
| Tomato Milk | CJ |
| Bean with Pork | CJ |
| Oyster Stew | CJ |

(i) Vegetables and Fruits

| Calorie Portion or Type | Calorie Letter Indication |
|---|---|
| Cooked Green Beans | E |
| Raw Vegetables | E |
| Boiled Vegetables | B |
| Raw Fruit | AC |
| Baked Potato | AC |
| Dried Beans | AC |
| Corn on Cob | AC |
| Cooked Fruit | AD |
| French Fries | AD |
| Sweet Potatoe | AD |
| Date | CE |
| Raisin | CE |
| Avacodos | CD |
| Pre-Sweet Cooked Fruits | CE |

10. The improvement as defined in claim 6 further comprising a plurality of fifth groups of contacts and whereby at least one of the fifth contacts indicates a plus and is electrically connected to the memory add circuit of the standard numerical calculator and at least one of the fifth contacts indicates an equal and is electrically connected to the equal circuit of the standard numerical calculator.

11. In a calculator of the type wherein a standard numerical electrical operative circuit is contained within a case, the circuit containing at least a memory add circuit and an equal circuit as well as other circuits and contacts, and has a plurality of pushbutton keys on the keyboard connected to a numerical readout so that a plurality of calculations, such as adding, subtracting, dividing and multiplying, may be made by pushing the appropriate pushbutton, the improvement comprising modifying the calculator keyboard and electrical circuit by providing a plurality of first, second and third groups of contacts and at least one fourth contact, whereby, (a) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;

(b) the plurality of second contacts are numerical in function and indicate pre-determined food and drink items and are electrically connected to the calculator electrical circuit in such a manner that each second contact has a pre-determined numerical value and each second contact is electrically connected in parallel to other similar second numerical contacts and to the similar first numerical contact in the standard numerical calculator;

(c) the plurality of third contacts are multiplier contacts and have located in proximity thereto indications of predetermined alphabetical letters corresponding to carbohydrate values of varying portions of food and drink items, the third contacts being electrically connected together and to the standard calculator circuit multiplier contact; and (d) the fourth contact is an equal contact in the electrical circuit and indicates the wording "carbohydrate".

12. The improvement as defined in claim 11 wherein the first contacts have visual alphabetical letters and are electrically connected to the calculator circuit as follows:

| Visual Letter | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |
| L | DECMIAL POINT |

13. The improvement as defined in claim 11 wherein the second contacts indicate food and drink items and are electrically connected to the calculator circuit as follows:

| Visual Item | Numerical Contact |
|---|---|
| Drinks | 4 |
| Bread, Cereals | 5 |
| Desserts | 5 |
| Fats, Oils, Dressing | 6 |
| Meats | 6 |
| Milk Products | 4 |
| Snacks | 5 |
| Soups | 8 |
| Vegetable, Fruits | 9 |

14. The improvement as defined in claim 11 wherein the third contacts indicate alphabetical letters corresponding to carbohydrate values of varying portions and/or types of food and drink items as follows:

(a) Drinks

| Carbohydrate Portion of type | Carbohydrate Letter Indication |
|---|---|
| Jigger 80 Proof Whiskey | K |
| Wine Glass Table Wine | A |
| Dessert Wine Fruit Flavor Drinks | E |
| Cola | J |
| Beer | J |
| Root Beer | J |
| Ginger Ale | J |
| Cider | D |
| Lemonade | D |

(b) Breads and Cereals

| Carbohydrate Portion or Type | Carbohydrate Letter Indication |
|---|---|
| Pretzel | A |
| Cracker | A |
| Pancake | C |
| Slice Bread | E |
| Cereals | E |
| Bran Cereal | G |
| Biscuit | G |
| Roll | G |
| Rice | B |
| Spaghetti & Meatballs | B |
| Waffle | B |

(c) Desserts and Sweets

| Carbohydrate Portion or Type | Carbohydrate Letter Indication |
|---|---|
| Hard Candy | C |
| Cookie | C |
| Fig Bar | E |
| Custard | E |
| Sirup | E |
| Jelly | E |
| Ice Cream | J |
| Angel Cake | B |
| Sherbet | B |
| Candy Bar | F |
| Pie | F |

(d) Fats, Oils and Dressings

| Carbohydrate Portion or Type | Carbohydrate Letter Indication |
|---|---|
| Mayonnaise | K |
| 1 Pat Butter | K |
| Salad Oil | K |
| Salad Dressing | LJ |
| Gravy | LJ |
| Peanut Butter | LJ |

(e) Meats

| Carbohydrate Portion or Type | Carbohydrate Letter Indication |
|---|---|
| Can Fish | K |
| Fowl | K |
| Lunch Meat | K |
| Corn Beef | K |
| Boil Egg | K |
| Steak/Chops | K |
| Clam | LJ |
| Egg Omelet | LJ |
| Bacon | LJ |
| Meatloaf | LJ |
| Sausage | LJ |
| Shrimp | A |
| Fried Fish | A |
| Oyster | C |
| Nuts | C |
| Liver | C |
| Chili | C |
| Beef Stew | C |
| Dried Beans | G |
| Pot Pies | G |

(f) Milk Products

| Carbohydrate Portion or Type | Carbohydrate Letter Indication |
|---|---|
| Slice Cheese | LC |
| Sour Cream | LC |
| Skim | C |
| Buttermilk | E |
| Whole | E |
| Condensed | E |
| Chocolate | J |
| Sherbet | B |
| Malt | B |
| Shake | B |

(g) Snacks

| Carbohydrate Portion or Type | Carbohydrate Letter Indication |
|---|---|
| Pickle | A |
| Olives | A |
| Popcorn | C |
| Potato Chips | E |
| French Fries | G |
| Corn Chips | G |
| Pizza | J |
| Donut | J |
| Hot Dog | J |
| Hamburger | J |

(h) Soups

| Carbohydrate Portion or Type | Carbohydrate Letter Indication |
|---|---|
| Bouillion | K |
| Broth | LJ |
| Chicken with Rice | A |
| Beef Noodle | A |
| Mushroom | A |
| Clam Chowder | C |
| Tomato | C |
| Vegetable | C |
| Bean | E |
| Pea | E |

(i) Vegetables and Fruits

| Carbohydrate Portion or Type | Carbohydrate Letter Indication |
| --- | --- |
| Raw Vegetables | LJ |
| Cooked Green Beans | LJ |
| Cooked Greens | A |
| Raw Fruit | C |
| Cooked Vegetables | C |
| Cooked Fruit | E |
| Dried Beans | E |
| Pre-Sweet Cooked Fruit | G |
| Sweet Potato | G |

15. The improvement as defined in claim 11 further comprising a plurality of fifth groups of contacts and whereby at least one of the fifth contacts indicates a plus and is electrically connected to the memory add circuit of the standard numerical calculator and at least one of the fifth contacts indicates an equal and is electrically connected to the equal circuit of the standard numerical calculator.

16. An improved method of determining the caloric value of food and/or drink as they are consumed, comprising the steps of:
(a) providing a caloric calculator having a visual readout and comprising a modified standard numerical circuit and having a plurality of first, second and third groups of contacts and at least a fourth contact whereby,
(1) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;
(2) the plurality of second contacts are numerical in function and indicate pre-determined food and drink items and are electrically connected to the calculator electrical circuit in such a manner that each second contact has a pre-determined numerical value and each second contact is electrically connected in parallel to other similar second numerical contacts and to the similar first numerical contact in the standard numerical calculator;
(3) the plurality of third contacts are multiplier contacts and have located in proximity thereto indications of predetermined alphabetical letters corresponding to caloric values of varying portions of food and drink items, the third contacts being electrically connected together and to the standard calculator circuit multiplier contact; and
(4) the fourth contact is an equal contact in the electrical circuit and indicates the wording "calorie";
(b) pushing a second contact corresponding to the food or drink to be consumed;
(c) pushing a third contact corresponding to the quantity or item of food or drink to be consumed;
(d) pushing a first contact corresponding to the alphabetical letter located in proximity to the third contact previously pushed; and
(e) pushing the fourth contact to complete the calculation and to view the caloric value on the visual readout of the calculator.

17. An improved method of determining the carbohydrate value of food and/or drink items as they are consumed, comprising the steps of:
(a) providing a carbohydrate calculator having a visual readout and comprising a modified standard numerical circuit and having a plurality of first, second and third groups of contacts and at least a fourth contact whereby,
(1) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;
(2) the plurality of second contacts are numerical in function and indicate pre-determined food and drink items and are electrically connected to the calculator electrical circuit in such a manner that each second contact has a pre-determined numerical value and each second contact is electrically connected in parallel to other similar second numerical contacts and to the similar first numerical contact in the standard numerical calculator;
(3) the plurality of third contacts are multiplier contacts and have located in proximity thereto indications of pre-determined alphabetical letters corresponding to carbohydrate values of varying portions of food and drink items, the third contacts being electrically connected together and to the standard calculator circuit multiplier contact; and
(4) the fourth contact is an equal contact in the electrical circuit and indicates the wording "carbohydrate";
(b) pushing a second contact corresponding to the food or drink to be consumed;
(c) pushing a third contact corresponding to the quantity or item or food or drink to be consumed;
(d) pushing a first contact corresponding to the alphabetical letter located in proximity to the third contact previously pushed; and
(e) pushing the fourth contact to complete the calculation and to view the carbohydrate value on the visual readout of the calculator.

18. A caloric and carbohydrate calculator, comprising:
(a) a case;
(b) a weighing mechanism contained within the case and having an exposed dial indicating varying combinations of alphabetical letters, the mechanism further having a weighing platform positioned on the exterior of the case;
(c) a standard numerical calculator electrical operation circuit contained within the case, the standard circuit containing at least a memory add circuit and an equal circuit as well as other circuits and contacts;
(d) a modified calculator keyboard having a plurality of first, second, third and fourth groups of contacts and whereby;
(1) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;

(2) the plurality of second contacts are numerical in function and indicate visually alphabetical letters corresponding to the alphabetical letters indicated on the exposed dial and are electrically connected to the calculator electrical circuit in such a manner that each second contact has a pre-determined numerical value and each second contact is electrically connected in parallel to the similar first numerical contact in the standard numerical calculator;

(3) the plurality of third contacts are multiplier contacts and have located in proximity thereto indications of pre-determined alphabetical letters corresponding to caloric and carbohydrate values of food and drink items which are also indicated, the third contacts being electrically connected together and to the standard calculator circuit multiplier contact;

(4) the plurality of fourth contacts are equal contacts in the electrical circuit and indicate the wording calories and carbohydrates; and (d) a standard numerical readout positioned in the calculator case and electrically connected to the circuit.

19. The calculator as defined in claim 18 wherein the first contacts have visual alphabetical letters and are electrically connected to the calculator circuit as follows:

| Visual Letter | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |
| L | DECMIAL POINT |

20. The calculator as defined in claim 18 wherein the second contacts indicate alphabetical letters and are electrically connected to the calculator circuit as follows:

| Visual Item | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |
| L | DECIMAL POINT |

21. The calculator as defined in claim 18 wherein the third contacts have indicated alphabetical letters and food and drink items corresponding to caloric and carbohydrate values of the food and drink items as follows:

(a) Drinks

| Calorie Portion or Type | Calorie Letter Indication | Carbohydrate Portion or type | Carbohydrate Letter Indication |
|---|---|---|---|
| Veg. Juice | E | Jigger 80 Proof Whiskey | K |
| Fruit Juice | AE | | |
| Table Wine | G | Table Wine | CLE |
| Jigger 80 Proof Whiskey | DB | Dessert Wine | G |
| | | Fruit Flavor | E |
| Ginger Ale | H | Cola | ELE |
| Dessert Wine | GK | Beer | ALJ |
| Cola | AG | Root Beer | ALJ |
| Beer | AC | Ginger Ale | CLD |
| Root Beer | AC | Cider | LEE |
| Fruit Flavor Drinks | AG | Lemonade | ELJ |

(b) Breads and Cereals

| Calorie Portion or Type | Calorie Letter Indication | Carbohydrate Portion or Type | Carbohydrate Letter Indication |
|---|---|---|---|
| Pretzel | FK | Pretzel | LA |
| Cracker | AEE | Cracker | JA |
| Slice Bread | DK | Pancake | LJE |
| Pancake | GK | Slice Bread | AC |
| Corn or Rice Cereals | AJ | Cereals | CK |
| | | Bran Cereal | AF |
| Grits | F | Biscuit | H |
| Roll | B | Roll | CK |
| Biscuit | JC | | |
| | | Rice | G |
| Rice | CE | | |
| | | Spaghetti & Meatballs | G |
| Wheat Cereal | AKJ | | |
| Pizza | FJ | Waffle | AK |
| Spaghetti & Meatballs | CF | | |
| Waffle | DK | | |

(c) Desserts and Sweets

| Calorie Portion or Type | Calorie Letter Indication | Carbohydrate Portion or Type | Carbohydrate Letter Indication |
|---|---|---|---|
| Hard Candy | AAK | Hard Candy | A |
| Angel Cake | AEJ | Cookie | EK |
| Sirup | HK | Fig Bar | AJ |
| Jellies | JD | Custard | E |
| Fig Bar | BJ | Sirup | AD |
| Fruit Cake | AAK | Jelly | AB |
| Cookie | AKK | Ice Cream | G |
| Custard | EK | Angel Cake | CC |
| Ice Cream | CF | Sherbet | J |
| Ginger Bread | AKK | Candy Bar | AB |
| Plain Cake with icing | AAE | Pie | D |
| Pie | JC | | |
| Pecan Pie | BB | | |
| Candy Bar | AGJ | | |

(d) Fats, Oils and Dressings

| Calorie Portion or Type | Calorie Letter Indication | Carbohydrate Portion or Type | Carbohydrate Letter Indication |
|---|---|---|---|
| Lo-Cal Dressing | EK | Mayonnaise | K |
| Home Cooked Salad Dressing | AJK | Butter | K |
| | | Salad Oil | K |
| Butter | AGK | | |

-continued

| Calorie Portion or Type | Calorie Letter Indication | Carbohydrate Portion or Type | Carbohydrate Letter Indication |
|---|---|---|---|
| | | Salad Dressing | G |
| Salad Dressing | AEK | | |
| | | Gravy | G |
| Gravy | CF | | |
| | | Peanut Butter | B |
| Mayonnaise | CKK | | |
| Peanut Butter | ACB | | |
| Salad Oil | CGK | | |

(e) Meats

| Calorie Portion or Type | Calorie Letter Indication | Carbohydrate Portion or Type | Carbohydrate Letter Indication |
|---|---|---|---|
| Egg | JK | Can Fish | K |
| Bacon | JC | Fowl | K |
| Clam | CC | Lunch Meat | K |
| Oyster | AJ | Corn Beef | K |
| Nuts | CDK | Boil Egg | K |
| Lunch Meat | FJ | Steak/Chops | K |
| Shrimp | EE | Clam | BLA |
| Broiled Fish | BD | Egg Omelet | C |
| Meatloaf | BJ | Bacon | A |
| Corned Beef | JC | Meatloaf | A |
| Beef Stew | AG | Sausage | A |
| Sausage | BE | Shrimp | A |
| Broiled Turkey, Chicken | JK | Fried Fish | C |
| | | Oyster | C |
| Fried Fish | JK | | |
| | | Nuts | C |
| Liver | BJ | | |
| | | Liver | A |
| Chili | EJ | | |
| | | Chili | E |
| Ham | FC | | |
| | | Beef Stew | E |
| Veal Cutlet | BC | | |
| | | Dried Beans | B |
| Lean Meats | DJ | | |
| | | Pot Pies | J |
| Meat with Fat | FJ | | |
| Steak/Chops | AAK | | |
| Pot Pies | JJ | | |

(f) Milk Products

| Calorie Portion or Type | Calorie Letter Indication | Carbohydrate Portion or Type | Carbohydrate Letter Indication |
|---|---|---|---|
| Buttermilk | AA | Slice Cheese | LJ |
| Skim Milk | AA | Sour Cream | A |
| Slice Cheese | AAJ | Skim | ALD |
| Yoghurt | AD | Buttermilk | ALD |
| Custard | JA | Whole | ALJ |
| Sherbet | CC | Condensed | E |
| Evaporated | JK | Chocolate | E |
| Whole | CK | Sherbet | HLE |
| Chocolate FLavor | CD | Malt | E |
| Sour Cream | JK | Shake | G |
| Cocoa | EK | | |
| Chocolate Soda | CK | | |
| Malt | EA | | |
| Chocolate Shake | GE | | |

(g) Snacks

| Calorie Portion or Type | Calorie Letter Indication | Carbohydrate Portion or Type | Carbohydrate Letter Indication |
|---|---|---|---|
| Chives | A | Pickle | A |
| Pickles | AK | Olives | C |
| Popcorn | AKF | Popcorn | EK |
| Potato Chips | CEK | Potato Chips | CK |
| French Fries | FK | French Fries | BLD |
| Corn Chips | FK | Corn Chips | CK |
| Pizza | FJ | Pizza | AG |
| Donut | ACD | Donut | AC |
| Hot Dog | AKK | Hot Dog | G |
| Hamburger | FJ | Hamburger | G |

(h) Soups

| Calorie Portion or Type | Calorie Letter Indication | Carbohydrate Portion or Type | Carbohydrate Letter Indication |
|---|---|---|---|
| Broth | AK | Bouillion | K |
| Chicken with Rice or Noodle | D | Broth | LD |
| | | Chicken with Rice | CLE |
| Vegetable | AA | | |
| Beef Noodle | H | Beef Noodle | C |
| Tomato | AC | Mushroom | E |
| Clam Chowder | AA | Clam Chowder | ELE |
| Asparagus | AG | Tomato | B |
| Minestrone | AG | Vegetable | GLE |
| Vegetable with Beef | AJ | Bean | BLE |
| | | Pea | F |
| Mushroom | AF | | |
| Split Pea | AF | | |
| Tomato Milk | CE | | |
| Bean with Pork | CE | | |
| Oyster Stew | AB | | |

(i) Vegetables and Fruits

| Calorie Portion or Type | Calorie Letter Indication | Carbohydrate Portion or Type | Carbohydrate Letter Indication |
|---|---|---|---|
| Green Beans | E | Raw Vegetables | C |
| Raw Vegetables | E | Green Beans | A |
| Boiled Vegetables | AK | Greens | LF |
| Raw Fruit | AD | Raw Fruit | G |
| | | Cooked Vegetables | C |
| Baked Potato | AJ | | |
| Dried Beans | AE | Cooked Fruit | B |
| Corn on Cob | AE | Dried Beans | D |
| Cooked Fruit | AD | Pre-Sweet Cooked Fruit | H |
| French Fries | FK | | |
| | | Sweet Potato | B |
| Sweet Potato | CD | | |
| Date | GJ | | |
| Raisin | AKD | | |
| Avocodos | EF | | |
| Pre-Sweet Cooked Fruits | CC | | |

22. The calculator as defined in claim 18 further comprising a plurality of fifth groups of contacts and whereby at least one of the fifth contacts indicates a plus and is electrically connected to the memory add circuit of the standard numerical calculator and at least one of the fifth contacts indicates an equal and is electrically connected to the equal circuit of the standard numerical calculator.

23. In a calculator of the type wherein a standard numerical electrical operative circuit is contained within a case, the circuit containing at least a memory add circuit and an equal circuit as well as other circuits and contacts, and has a plurality of pushbutton keys on the keyboard connected to a numerical readout so that a plurality of calculations, such as adding, subtracting, dividing and multiplying, may be made by pushing the appropriate pushbutton, the improvement comprising modifying the calculator keyboard and electrical circuit by providing a plurality of first, second and third groups of contacts and at least one fourth contact, whereby, (a) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;

(b) the plurality of second contacts are numerical in function and indicate visually alphabetical letters and are electrically connected to the calculator electrical circuit in such a manner that each second contact has a predetermined numerical value and each second contact is electrically connected in parallel to the similar first numerical contact in the standard numerical calculator;

(c) the plurality of third contacts are multiplier contacts and have located in proximity thereto indications of predetermined alphabetical letters corresponding to caloric values of varying food and drink items which are also indicated, the third contacts being electrically connected together and to the standard calculator circuit multiplier contact; and (d) the fourth contact is an equal contact in the electrical circuit and indicates the wording "calorie".

24. The improvement as defined in claim 23 wherein the first contacts have visual alphabetical letters and are electrically connected to the calculator circuit as follows:

| Visual Letter | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |
| L | DECMIAL POINT |

25. The improvement as defined in claim 23 wherein the second contacts indicate alphabetical letters and are electrically connected to the calculator circuit as follows:

| Visual Item | Numerical Contact |
|---|---|
| A | 1 |
| B | 6 |
| C | 2 |
| D | 7 |
| E | 3 |
| F | 8 |
| G | 4 |
| H | 9 |
| J | 5 |
| K | 0 |
| L | DECIMAL POINT |

26. The improvement as defined in claim 23 wherein the third contacts have indicated alphabetical letters and food and drink items corresponding to caloric values of the food and drink items as follows:

(a) Drinks

| Calorie Portion or Type | Calorie Letter Indication |
|---|---|
| Veg. Juice | E |
| Fruit Juice | AE |
| Table Wine | G |
| Jigger 80 Proof Whiskey | DB |
| Ginger Ale | H |
| Dessert Wine | GK |
| Cola | AG |
| Beer | AC |
| Root Beer | AC |
| Fruit Flavor Drinks | AG |

(b) Breads and Cereals

| Calorie Portion or Type | Calorie Letter Indication |
|---|---|
| Pretzel | FK |
| Cracker | AEE |
| Slice Bread | DK |
| Pancake | GK |
| Corn or Rice Cereals | AJ |
| Grits | F |
| Roll | B |
| Biscuit | JC |
| Rice | CE |
| Wheat Cereal | AKJ |
| Pizza | FJ |
| Spaghetti & Meatballs | CF |
| Waffle | DK |

(c) Desserts and Sweets

| Calorie Portion or Type | Calorie Letter Indication |
|---|---|
| Hard Candy | AAK |
| Angel Cake | AEJ |
| Sirup | HK |
| Jellies | JD |
| Fig Bar | BJ |
| Fruit Cake | AAK |
| Cookie | AKK |
| Custard | EK |
| Ice Cream | CF |
| Ginger Bread | AKK |
| Plain Cake with Icing | AAE |
| Pie | JC |
| Pecan Pie | BB |
| Candy Bar | AGJ |

(d) Fats, Oils, Dressings

(e) Meats (continued)

| Calorie Portion or Type | Calorie Letter Indication |
|---|---|
| Lo-Cal Dressing Home Cooked Salad Dressing | EK |
| | AJK |
| Butter | AGK |
| Salad Dressing | AEK |
| Gravy | CF |
| Mayonnaise | CKK |
| Peanut Butter | ACB |
| Salad Oil | CGK |

(e) Meats

| Calorie Portion or Type | Calorie Letter Indication |
|---|---|
| Egg | JK |
| Bacon | JC |
| Clam | CC |
| Oyster | AJ |
| Nuts | CDK |
| Lunch Meat | FJ |
| Shrimp | EE |
| Broiled Fish | BD |
| Meatloaf | BJ |
| Corned Beef | JC |
| Beef Stew | AG |
| Sausage | BE |
| Broiled Turkey, Chicken | JK |
| Fried Fish | JK |
| Liver | BJ |
| Chili | EJ |
| Ham | FC |
| Veal Cutlet | BC |
| Lean Meats | DJ |
| Meat with Fat | FJ |
| Steaks/Chops | AAK |
| Pot Pies | JJ |

(f) Milk Products

| Calorie Portion or Type | Calorie Letter Indication |
|---|---|
| Buttermilk | AA |
| Skim Milk | AA |
| Slice Cheese | AAJ |
| Yoghurt | AD |
| Custard | JA |
| Sherbet | CC |
| Evaporated | JK |
| Whole | CK |
| Chocolate Flavor | CD |
| Sour Cream | JK |
| Cocoa | EK |
| Chocolate Soda | CK |
| Malt | EA |
| Chocolate Shake | GE |

(g) Snacks

| Calorie Portion or Type | Calorie Letter Indication |
|---|---|
| Chives | A |
| Pickles | AK |
| Popcorn | AKF |
| Potato Chips | CEK |
| French Fries | FK |
| Corn Chips | FK |
| Pizza | FJ |
| Donut | ACD |
| Hot Dog | AKK |
| Hamburger | FJ |

(h) Soups

| Calorie Portion or Type | Calorie Letter Indication |
|---|---|
| Broth | AK |
| Chicken with Rice or Noodle | D |
| Vegetable | AA |
| Beef Noodle | H |
| Tomato | AC |
| Clam Chowder | AA |
| Asparagus | AG |
| Minestrone | AG |
| Vegetable with Beef | AJ |
| Mushroom | AF |
| Split Pea | AF |
| Tomato Milk | CE |
| Bean with Pork | CE |
| Oyster Stew | AB |

(i) Vegetables and Fruits

| Calorie Portion or Type | Calorie Letter Indication |
|---|---|
| Green Beans | E |
| Raw Vegetables | E |
| Boiled Vegetables | AK |
| Raw Fruit | AD |
| Baked Potato | AJ |
| Dried Beans | AE |
| Corn on Cob | AE |
| Cooked Fruit | AD |
| French Fries | FK |
| Sweet Potato | CD |
| Date | GJ |
| Raisin | AKD |
| Avocados | EF |
| Pre-Sweet Cooked Fruits | CC |

27. The improvement as defined in claim 23 further comprising a plurality of fifth groups of contacts and whereby at least one of the fifth contacts indicates a plus and is electrically connected to the memory add circuit of the standard numerical calculator and at least one of the fifth contacts indicates an equal and is electrically connected to the equal circuit of the standard numerical calculator.

28. In a calculator of the type wherein a standard numerical electrical operative circuit is contained within a case, the circuit containing at least a memory add circuit and an equal circuit as well as other circuits and contacts, and has a plurality of pushbutton keys on the keyboard connected to a numerical readout so that a plurality of calculations, such as adding, subtracting, dividing and multiplying, may be made by pushing the appropriate pushbutton, the improvement comprising modifying the calculator keyboard and electrical circuit by providing a plurality of first, second and third groups of contacts and at least one fourth contact, whereby, (a) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;

(b) the plurality of second contacts are numerical in function and indicate visually alphabetical letters and are electrically connected to the calculator electrical circuit in such a manner that each second contact has a pre-determined numerical value and each second contact is electrically connected in parallel to the similar first numerical contact in the standard numerical calculator;

(c) the plurality of third contacts are multiplier contacts and have located in proximity thereto indications of pre-determined alphabetical letters corresponding to carbohydrate values of food and drink items which are also indicated, the third contacts being electrically connected together and to the standard calculator circuit multiplier contact; and (d) the fourth contact is an equal contact in the electrical circuit and indicates the wording "carbohydrate".

29. The improvement as defined in claim 28 wherein the first contacts have visual alphabetical letters and are electrically connected to the calculator circuit as follows:

| Visual Letter | Numerical Contact |
| --- | --- |
| A | 1 |
| B | 6 |
| C | 2 |
| D | 7 |
| E | 3 |
| F | 8 |
| G | 4 |
| H | 9 |
| J | 5 |
| K | 0 |
| L | DECMIAL POINT |

30. The improvement as defined in claim 28 wherein the second contacts indicate alphabetical letters and are electrically connected to the calculator circuit as follows:

| Visual Letter | Numerical Contact |
| --- | --- |
| A | 1 |
| B | 6 |
| C | 2 |
| D | 7 |
| E | 3 |
| F | 8 |
| G | 4 |
| H | 9 |
| J | 5 |
| K | 0 |
| L | DECMIAL POINT |

31. The improvement as defined in claim 28 wherein the third contacts have indicated alphabetical letters and food and drink items corresponding to carbohydrate values of the food and drink items as follows:

(a) Drinks

| Carbohydrate Portion or Type | Carbohydrate Letter Indication |
| --- | --- |
| Jigger 80 Proof Whiskey | K |
| Table Wine | CLE |
| Dessert Wine | G |
| Fruit Flavor | E |
| Cola | ELE |
| Beer | ALJ |
| Root Beer | ALJ |
| Ginger Ale | CLD |
| Cider | LEE |
| Lemonade | ELJ |

(b) Breads and Cereals

| Carbohydrate Portion or Type | Carbohydrate Letter Indication |
| --- | --- |
| Pretzel | LA |
| Cracker | JA |
| Pancake | LJE |
| Slice Bread | AC |
| Cereals | CK |
| Bran Cereal | AF |
| Biscuit | H |
| Roll | CK |
| Rice | G |
| Spaghetti & Meatballs | G |
| Waffle | AK |

(c) Desserts and Sweets

| Carbohydrate Portion or Type | Carbohydrate Letter Indication |
| --- | --- |
| Hard Candy | A |
| Cookie | EK |
| Fig Bar | AJ |
| Custard | E |
| Sirup | AD |
| Jelly | AB |
| Ice Cream | G |
| Angel Cake | CC |
| Sherbet | J |
| Candy Bar | AB |
| Pie | D |

(d) Fats, Oils and Dressings

| Carbohydrate Portion or Type | Carbohydrate Letter Indication |
| --- | --- |
| Mayonnaise | K |
| Butter | K |
| Salad Oil | K |
| Salad Dressing | G |
| Gravy | G |
| Peanut Butter | B |

(e) Meats

| Carbohydrate Portion or Type | Carbohydrate Letter Indication |
| --- | --- |
| Can Fish | K |
| Fowl | K |
| Lunch Meat | K |

-continued

| Carbohydrate Portion or Type | Carbohydrate Letter Indication |
|---|---|
| Corn Beef | K |
| Boil Egg | K |
| Steak/Chops | K |
| Clam | BLA |
| Egg Omelet | C |
| Bacon | A |
| Meatloaf | A |
| Sausage | A |
| Shrimp | A |
| Fried Fish | C |
| Oyster | C |
| Nuts | C |
| Liver | A |
| Chili | E |
| Beef Stew | E |
| Dried Beans | B |
| Pot Pies | J |

(f) Milk Products

| Carbohydrate Portion or Type | Carbohydrate Letter Indication |
|---|---|
| Slice Cheese | LJ |
| Sour Cream | A |
| Skim | ALD |
| Buttermilk | ALD |
| Whole | ALJ |
| Condensed | E |
| Chocolate | E |
| Sherbet | HLE |
| Malt | E |
| Shake | G |

(g) Snacks

| Carbohydrate Portion or Type | Carbohydrate Letter Indication |
|---|---|
| Pickle | A |
| Olives | C |
| Popcorn | EK |
| Potato Chips | CK |
| French Fries | BLD |
| Corn Chips | CK |
| Pizza | AG |
| Donut | AC |
| Hot Dog | G |
| Hamburger | G |

(h) Soups

| Carbohydrate Portion or Type | Carbohydrate Letter Indication |
|---|---|
| Bouillion | K |
| Broth | LD |
| Chicken with Rice | CLE |
| Beef Noodle | C |
| Mushroom | E |
| Clam Chowder | ELE |
| Tomato | B |
| Vegetable | GLE |
| Bean | BLE |
| Pea | F |

(i) Vegetables and Fruits

| Carbohydrate Portion or Type | Carbohydrate Letter Indication |
|---|---|
| Raw Vegetables | C |
| Green Beans | A |
| Greens | LF |
| Raw Fruit | G |
| Cooked Vegetables | C |
| Cooked Fruit | B |
| Dried Beans | D |
| Pre-Sweet Cooked Fruit | H |
| Sweet Potato | B |

32. The improvement as defined in claim 28 further comprising a plurality of fifth groups of contacts and whereby at least one of the fifth contacts indicates a plus and is electrically connected to the memory add circuit of the standard numerical calculator and at least one of the fifth contacts indicates an equal and is electrically connected to the equal circuit of the standard numerical calculator.

33. An improved method of determining the caloric value of food and/or drink as they are consumed, comprising the steps of:

(a) providing a case with a weighing mechanism contained therein and having an exposed dial indicating varying combinations of alphabetical letters, the mechanism further having a weighing platform positioned on the exterior of the case;

(b) providing a caloric calculator within the case and having a visual readout and comprising a modified standard numerical circuit and having a plurality of first, second and third groups of contacts and at least a fourth contact whereby, (1) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;

(2) the plurality of second contacts are numerical in function and indicate visually alphabetical letters corresponding to the alphabetical letters indicated on the exposed dial and and are electrically connected to the calculator electrical circuit in such a manner that each second contact has a predetermined numerical value and each second contact is electrically connected in parallel to the similar first numerical contact in the standard numerical calculator;

(3) the plurality of third contacts are multiplier contacts representing varying food and drink catagories and have located in proximity thereto indications of predetermined alphabetical letters corresponding to caloric values of food and drink items which are also indicated, the third contacts being electrically connected together and to the standard calculator circuit multiplier contact; and (4) the fourth contact is an equal contact in the electrical circuit and indicates the wording "calorie";

(c) placing a predetermined amount of food or drink item on the platform and reading a combination of alphabetical letters on the weighing mechanism;

(d) pushing a group of second contacts corresponding to the weight scale indication of combinations of alphabetical letters;

(e) pushing a third contact corresponding to the catagory of food or drink being weighed;

(f) pushing a first contact or contacts corresponding to the alphabetical letter of the exact food and drink item being weighed shown located in proximity to the third contact previously pushed; and (g) pushing the fourth contact to complete the calculation and to view the caloric value on the visual readout of the calculator.

34. An improved method of determining the carbohydrate value of food and/or drink items as they are consumed, comprising the steps of:

(a) providing a case with a weighing mechanism contained therein and having an exposed dial indicating varying combinations of alphabetical letters, the mechanism further having a weighing platform positioned on the exterior of the case;

(b) providing a carbohydrate calculator within the case and having a visual readout and comprising a modified standard numerical circuit and having a plurality of first, second and third groups of contacts and at least a fourth contact whereby, (1) the plurality of first contacts are numerical in function and indicate visually alphabetical letters and are electrically connected to the standard numerical calculator electrical circuit so that each visual alphabetical letter represents and contacts, when pushed, a different numeral from 0 to 9 in the calculator electrical circuit;

(2) the plurality of second contacts are numerical in function and indicate visually alphabetical letters corresponding to the alphabetical letters indicated on the exposed dial and are electrically connected to the calculator electrical circuit in such a manner that each second contact has a pre-determined numerical value and each second contact is electrically connected in parallel to the similar first numerical contact in the standard numerical calculator;

(3) the plurality of third contacts are multiplier contacts representing varying food and drink catagories and have located in proximity thereto indications of pre-determined alphabetical letters corresponding to carbohydrate values of food and drink items which are also indicated, the third contacts being electrically connected together and to the standard calculator circuit multiplier contact; and (4) the fourth contact is an equal contact in the electrical circuit and indicates the wording "carbohydrate";

(c) placing a predetermined amount of food or drink item on the platform and reading a combination of alphabetical letters on the weighing mechanism;

(d) pushing a group of second contacts corresponding to the weight scale indication of combinations of alphabetical letters;

(e) pushing a third contact corresponding to the catagory or food or drink being weighed;

(f) pushing a first contact or contacts corresponding to the alphabetical letter of the exact food or drink item being weighed shown located in proximity to the third contact previously pushed; and (g) pushing the fourth contact to complete the calculation and to view the caloric value on the visual readout of the calculator.

* * * * *